(12) United States Patent
Harrington et al.

(10) Patent No.: US 11,491,297 B2
(45) Date of Patent: Nov. 8, 2022

(54) HUMIDIFIER FOR A RESPIRATORY THERAPY DEVICE

(71) Applicant: RESMED PTY LTD, Bella Vista (AU)

(72) Inventors: Matthew Rolf Harrington, Gosford (AU); Andrew Chan, Sydney (AU); Luke Andrew Stanislas, Sydney (AU); Nan Hai Wu, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 499 days.

(21) Appl. No.: 16/476,373

(22) PCT Filed: Jan. 9, 2018

(86) PCT No.: PCT/AU2018/050007
§ 371 (c)(1),
(2) Date: Jul. 8, 2019

(87) PCT Pub. No.: WO2018/126299
PCT Pub. Date: Jul. 12, 2018

(65) Prior Publication Data
US 2020/0114114 A1    Apr. 16, 2020

(30) Foreign Application Priority Data
Jan. 9, 2017  (AU) ............................... 2017900037

(51) Int. Cl.
*A61M 16/16* (2006.01)
*A61M 11/04* (2006.01)
(Continued)

(52) U.S. Cl.
CPC ........ *A61M 16/161* (2014.02); *A61M 11/042* (2014.02); *A61M 15/0003* (2014.02);
(Continued)

(58) Field of Classification Search
CPC .............. A61M 16/161; A61M 11/042; A61M 15/0003; A61M 16/125; A61M 16/06;
(Continued)

(56) References Cited

U.S. PATENT DOCUMENTS 1,960,098 A * 5/1934 Breitenbach ............ F24F 6/025
D23/360
4,782,832 A  11/1988 Trimble et al.
(Continued)

FOREIGN PATENT DOCUMENTS

WO    98/004310    2/1998
WO    98/034665    8/1998
(Continued)

OTHER PUBLICATIONS

"*Respiratory Physiology*", by John B. West, Lippincott Williams & Wilkins, 9th edition published 2012 (8 pages).
(Continued)

*Primary Examiner* — Charles S Bushey
(74) *Attorney, Agent, or Firm* — Nixon & Vanderhye P.C.

(57) ABSTRACT

An apparatus for humidification of air to be delivered to a patient's airways may include a reservoir, and a humidifier chamber. The humidifier chamber may include a humidifier wick and a heating element for heating the humidifier chamber. The humidifier wick may comprise a fibrous sheet material. The humidifier chamber and wick may be vertically oriented in use such that a first end of the wick is above the second end of the wick. A deioniser may be provided to deionise the liquid prior to the humidifier wick. The apparatus may pasteurise liquid to be delivered to the humidification wick.

18 Claims, 17 Drawing Sheets

(51) Int. Cl.
*A61M 15/00* (2006.01)
*A61M 16/12* (2006.01)
*A61M 16/06* (2006.01)
*F24F 6/04* (2006.01)
*A61M 16/00* (2006.01)
*F24F 6/00* (2006.01)

(52) U.S. Cl.
CPC .......... *A61M 16/06* (2013.01); *A61M 16/125* (2014.02); *A61M 16/162* (2013.01); *F24F 6/043* (2013.01); *A61M 2016/0027* (2013.01); *A61M 2016/0039* (2013.01); *A61M 2202/0208* (2013.01); *A61M 2205/3334* (2013.01); *F24F 2006/008* (2013.01)

(58) Field of Classification Search
CPC ........ A61M 16/162; A61M 2016/0027; A61M 2016/0039; A61M 2202/0208; A61M 2205/3334; F24F 6/043; F24F 2006/008; F24F 6/08; F24F 6/10
USPC ....... 261/104, 107, 142; 128/203.27, 204.13, 128/204.18
See application file for complete search history.

(56) References Cited

U.S. PATENT DOCUMENTS

| | | | |
|---|---|---|---|
| 4,944,310 A | 7/1990 | Sullivan | |
| 5,687,715 A | 11/1997 | Landis | |
| 6,010,118 A * | 1/2000 | Milewicz | A61M 16/1085 128/205.12 |
| 6,474,628 B1 * | 11/2002 | Stroh | F24F 6/04 261/99 |
| 6,532,959 B1 | 3/2003 | Berthon-Jones | |
| 6,581,594 B1 | 6/2003 | Drew et al. | |
| 7,717,404 B2 * | 5/2010 | Hasegawa | B01J 47/12 261/104 |
| 7,866,944 B2 | 1/2011 | Kenyon et al. | |
| 7,992,554 B2 * | 8/2011 | Radomski | A61M 16/147 392/394 |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 10,518,061 B2 * | 12/2019 | Harrington | A61M 16/06 |
| 10,864,346 B2 * | 12/2020 | Harrington | A61M 16/109 |
| 2003/0211799 A1 | 11/2003 | Yao et al. | |
| 2006/0213646 A1 | 9/2006 | Hsu | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0083965 A1 * | 4/2010 | Virr | A61M 16/142 128/203.26 |
| 2014/0352345 A1 | 12/2014 | Hakbijl et al. | |
| 2015/0270561 A1 * | 9/2015 | Harenbrock | H01M 8/04149 261/104 |
| 2017/0000968 A1 * | 1/2017 | Harrington | A61M 16/06 |
| 2018/0056024 A1 * | 3/2018 | Harrington | A61M 16/161 |
| 2020/0078549 A1 * | 3/2020 | Harrington | A61M 16/026 |
| 2020/0384236 A1 * | 12/2020 | Harrington | A61M 16/162 |

FOREIGN PATENT DOCUMENTS

| | | |
|---|---|---|
| WO | 2000/078381 | 12/2000 |
| WO | 2004/073778 | 9/2004 |
| WO | 2005/063328 | 7/2005 |
| WO | 2006/074513 | 7/2006 |
| WO | 2006/130903 | 12/2006 |
| WO | 2009/052560 | 4/2009 |
| WO | 2010/135785 | 12/2010 |
| WO | 2012/171072 | 12/2012 |
| WO | 2013/020167 | 2/2013 |
| WO | 2015/135040 | 9/2015 |
| WO | 2016/139645 | 9/2016 |
| WO | 2016/191806 | 12/2016 |

OTHER PUBLICATIONS

International Search Report dated Feb. 26, 2018 in International Application No. PCT/AU2018/050007 (6 pages).
Written Opinion dated Feb. 26, 2018 in International Application No. PCT/AU2018/050007 (4 pages).
Written Opinion dated Nov. 5, 2018 in International Application No. PCT/AU2018/050007 (4 pages).
International Preliminary Report on Patentability dated Apr. 26, 2019 in International Application No. PCT/AU2018/050007 (13 pages).

* cited by examiner

HUMIDIFIER FOR A RESPIRATORY THERAPY DEVICE

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/AU2018/050007 filed Jan. 9, 2018 which designated the U.S. and claims the benefit of Australian Provisional Application No. AU 2017900037, filed Jan. 9, 2017, the entire contents of each of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

Respiratory humidifiers are available in many forms and may be a standalone device that is coupled to an RPT device via an air conduit, may be integrated with the RPT device, or may be configured to be directly coupled to the relevant RPT device. While known passive humidifiers can provide some relief, generally a heated humidifier may be used to provide sufficient humidity and temperature to the air so that the patient will be comfortable. Humidifiers may comprise a water reservoir or tub having a capacity of several hundred millilitres (ml), a heating element for heating the water in the reservoir, a control to enable the level of humidification to be varied, a gas inlet to receive gas from the RPT device, and a gas outlet adapted to be connected to an air circuit that delivers the humidified gas to the patient interface.

Heated passover humidification is one exemplary form of humidification used with an RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 RPT devices respectively.

Other humidifiers may also be used such as a bubble or diffuser humidifier or a jet humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

One example of a prior art humidifier comprises a reservoir to retain a volume of liquid (e.g. water), a humidifier inlet to receive a flow of air, and a humidifier outlet to deliver a humidified flow of air. In some forms, an inlet and an outlet of the reservoir may be the humidifier inlet and the humidifier outlet respectively. The reservoir may be a removable component of the humidifier. The humidifier may further comprise a humidifier dock, which may be adapted to receive the reservoir and comprise a heating element. The reservoir may comprise a conductive plate configured to allow efficient transfer of heat from the heating element to the volume of liquid in the reservoir.

Thus, in such a form, the reservoir contains the entire volume of water to be used to humidify the flow of air, and receives the flow of air to pass over the water and delivers the humidified flow of air. Accordingly, such a humidifier configuration presents a number of challenges, including: risk of spillage of the volume of water (e.g. into the RPT device or to the patient), achieving adequate humidification output, high thermal mass of the volume of water and changes to thermal mass according to changes in water volume present in the reservoir. Due to these challenges, many prior art humidifiers may suffer from one or more of: long warm-up time and cool-down time, slow response time (e.g. to a change in desired humidification output), change to response time throughout a therapy session and large size. The large size may manifest itself in terms of volume and/or footprint (i.e. surface area covered by the humidifier, or effectively covered by the humidifier as to become inaccessible), which may make the humidifier less suited for placement on a bedside table for example. A humidifier according to the present technology seeks to improve upon, or ameliorate, one or more of the above characteristics

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

One aspect of the present technology relates to an apparatus to change the absolute humidity of a flow of air for delivery to an entrance of the airways of a patient, said change being compared to the absolute humidity of ambient air. The apparatus may comprise a reservoir configured to hold a first volume of liquid. The apparatus may comprise a humidifier chamber. The humidifier chamber may comprise an air inlet for receiving the flow of air. The humidifier chamber may comprise a humidifier wick configured to retain a second volume of liquid from the reservoir. The humidifier chamber may comprise a heating element configured to heat the humidifier wick to vapourise the second volume of liquid to add absolute humidity to the flow of air. The humidifier wick may comprise a fibrous sheet material, the fibrous sheet material further comprising a fabric woven of fibres.

One aspect of the present technology relates to a wick for positioning within a humidifier chamber of an apparatus to change the absolute humidity of a flow of air for delivery to an entrance of the airways of a patient, said change being compared to the absolute humidity of ambient air, configured to retain a volume of water, wherein the humidifier wick comprises a fibrous sheet material, the fibrous sheet material further comprising a fabric woven of fibres.

In further examples of the aspects of the present technology described in the two preceding paragraphs: (a) the fibrous sheet material may be configured to provide a capillary action to distribute water through the wick and retain it therein, (b) the fibrous sheet material may comprise a fabric woven of fibres, (c) the fibrous sheet material may comprise different types of fibre, (d) the fibrous sheet material may comprise a first plurality of fibres and a second plurality of fibres, wherein the first plurality of fibres are each greater in thickness than each of the second plurality of fibres, (e) the fibrous sheet material may be configured such that the relatively thicker fibres are provided closer to a heating element of the apparatus, and the thinner fibres provided closer to the flow of air, (f) the fibrous sheet material may comprise a first layer comprising the relatively thicker fibres, and a second layer comprising the thinner fibres, (g) the fibrous sheet material may comprise a mono-multi woven fabric, (h) the fibrous sheet material may comprise a mono-mono woven fabric, (i) the wick may be tubular in shape, and/or (j) the humidifier chamber and wick may be vertically oriented in use such that a first end of the wick is above the second end of the wick.

One aspect of the present technology relates to an apparatus to change the absolute humidity of a flow of air for delivery to an entrance of the airways of a patient, said change being compared to the absolute humidity of ambient air. The apparatus may comprise a reservoir configured to hold a first volume of liquid. The apparatus may comprise a humidifier chamber. The humidifier chamber may comprise an air inlet for receiving the flow of air. The humidifier chamber may comprise a humidifier wick configured to retain a second volume of liquid from the reservoir. The humidifier chamber may comprise a heating element configured to heat the humidifier wick to vapourise the second volume of liquid to add absolute humidity to the flow of air. The humidifier chamber and wick may be vertically oriented in use such that a first end of the wick is above the second end of the wick.

One aspect of the present technology relates to a humidifier chamber for use with a humidifier for increasing an absolute humidity of a flow of air to be delivered to a patient's airways, the humidifier comprising a reservoir configured to retain a first volume of water. The humidifier chamber may comprise an air inlet for receiving the flow of air. The humidifier chamber may comprise a humidifier wick configured to receive and retain a second volume of water from the reservoir and substantially enclosing a path therethrough for the flow of air. The humidifier chamber may comprise an air outlet for delivering the flow of air. The humidifier chamber may be configured to be secured to a heating element configured to heat the humidifier wick to vaporise the second volume of water to add absolute humidity to the flow of air. The humidifier chamber and wick may be vertically oriented in use such that a first end of the wick is above the second end of the wick.

In further examples of the aspects of the present technology described in the two preceding paragraphs: (a) a water feed inlet may be provided at the first end of the wick, (b) the water feed inlet may be provided at the second end of the wick, (c) the reservoir may be fluidly connected to the wick via a pre-delivery chamber, (d) the pre-delivery chamber may comprise an annular chamber, (e) the pre-delivery chamber may comprise at least one lateral outlet to the wick, (f) the pre-delivery chamber may comprise a depression below the lateral outlet, (g) the depression of the pre-delivery chamber may pitch up towards the lateral outlet, (h) the pre-delivery chamber may be provided between an air flow baffle provided within the humidifier chamber and at least one interior surface of the humidifier chamber, and/or (i) the apparatus may comprise a deioniser configured to deionise the liquid prior to vapourisation of the liquid.

One aspect of the present technology relates to an apparatus to change the absolute humidity of a flow of air for delivery to an entrance of the airways of a patient, said change being compared to the absolute humidity of ambient air. The apparatus may comprise a reservoir configured to hold a first volume of liquid. The apparatus may comprise a heating element to create vapour from the liquid. The apparatus may comprise a humidifier chamber to mix the flow of air with the vapour. The apparatus may comprise a deioniser configured to deionise the liquid prior to vapourisation of the liquid.

One aspect of the present technology relates to a deionisation cartridge configured to be provided within a reservoir configured to hold a volume of liquid of an apparatus for changing the absolute humidity of a flow of air for delivery to an entrance of the airways of a patient, the change being compared to the absolute humidity of ambient air.

In further examples of the aspects of the present technology described in the two preceding paragraphs: (a) the deioniser may be provided within the reservoir, (b) the deioniser may comprise at least one ion exchange resin as the medium by which deionisation is achieved, (c) the deionisation medium may comprise a first type of resin configured to remove positively charged ions and a second type of resin configured to remove negatively charged ions (d) the first and second types of resin may be provided in separate stages, (e) the first and second types of resin may be mixed in a single stage, (f) the deioniser may comprise a deioniser cartridge configured to hold the at least one ion exchange resin, (g) the deioniser cartridge may be configured to be removably positioned within the reservoir, (h) the deioniser cartridge may comprise a base portion having a cartridge outlet, (i) the deioniser cartridge may comprise a first end wall and second end wall extending from distal ends of the base portion, joined by a first side wall and second side wall, (j) the deioniser cartridge may comprise at least one baffle extending from the base portion, (k) the deioniser cartridge may comprise a lid provided to produce a cavity within which the at least ion exchange resin is positioned, (l) the lid may comprise a cartridge inlet toward a corner distal from the cartridge outlet, (m) the deioniser cartridge may be configured to provide a draft along an outer surface of the lid leading to the cartridge inlet, (n) the deioniser cartridge may be configured to provide a draft along the base portion between the cartridge inlet and the cartridge outlet, (o) the deioniser cartridge may comprise a filter frame at the cartridge outlet, (p) a filter may be secured to the filter frame, and/or (q) the apparatus may be configured to pasteurise liquid to be delivered to the humidifier wick.

One aspect of the present technology relates to an apparatus to change the absolute humidity of a flow of air for delivery to an entrance of the airways of a patient, said change being compared to the absolute humidity of ambient air. The apparatus may comprise a reservoir configured to hold a first volume of liquid. The apparatus may comprise a humidifier chamber. The humidifier chamber may comprise an air inlet for receiving the flow of air. The humidifier chamber may comprise a humidifier wick configured to retain a second volume of liquid from the reservoir. The humidifier chamber may comprise a heating element configured to heat the humidifier wick to vapourise the second volume of liquid to add absolute humidity to the flow of air. The apparatus may be configured to pasteurise liquid to be delivered to the humidifier wick.

In further examples of the aspect of the present technology described in the preceding paragraph: (a) the apparatus may be configured to heat at least a portion of a water delivery conduit between the reservoir and the humidifier wick, (b) the water delivery conduit may be thermally coupled to the heating element configured to create the vapour, (c) the apparatus may comprise a dedicated pasteurisation heating element, (d) the apparatus may comprise a controller configured to implement a cleaning mode, in which normal operation of the apparatus is suspended, (e) the cleaning mode may be initiated periodically, (f) the cleaning mode may be initiated on detection of conditions which indicate that the apparatus is not in demand and it is safe to initiate the cleaning mode, (g) the cleaning mode may be initiated on insertion of a component into the apparatus, (h) the component may be a sealing member configured to seal an outlet of the apparatus after the mixing of the flow of air with the vapour, and/or (i) the cleaning mode may be initiated on receiving a user input.

One aspect of the present technology relates to a method of humidifying a supply of air for delivery to an entrance of an airway of a patient. The method may comprise delivering liquid from a reservoir configured to hold a first volume of liquid to a humidifier wick of a humidifier chamber. The method may comprise heating the humidifier wick to vapourise the liquid to add absolute humidity to a flow of air through the humidifier chamber. The method may comprise pasteurising the liquid prior to arriving at the humidifier wick.

In further examples of the aspect of the present technology described in the preceding paragraph: (a) the method may further comprise heating at least a portion of a water delivery conduit between the reservoir and the humidifier wick, (b) the method may comprise implementing a cleaning mode, in which normal operation of the apparatus is suspended, (c) the cleaning mode may be initiated periodically, (d) the cleaning mode may be initiated on detection of conditions which indicate that the apparatus is not in demand and it is safe to initiate the cleaning mode, (e) the cleaning mode may be initiated on insertion of a component into the apparatus, (f) the component may be a sealing member configured to seal an outlet of the apparatus after the mixing of the flow of air with the vapour, and/or (g) the cleaning mode may be initiated on receiving a user input.

One aspect of the present technology relates to a device for treating a respiratory disorder. The device may comprise a Positive Airway Pressure generator. The device may comprise an apparatus substantially as described herein.

The methods/systems/devices/apparatus described herein can provide improved functioning in a processor, such as of a processor of a specific purpose computer, respiratory monitor and/or a respiratory therapy apparatus. Moreover, the methods/devices/apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

Figure 1A:
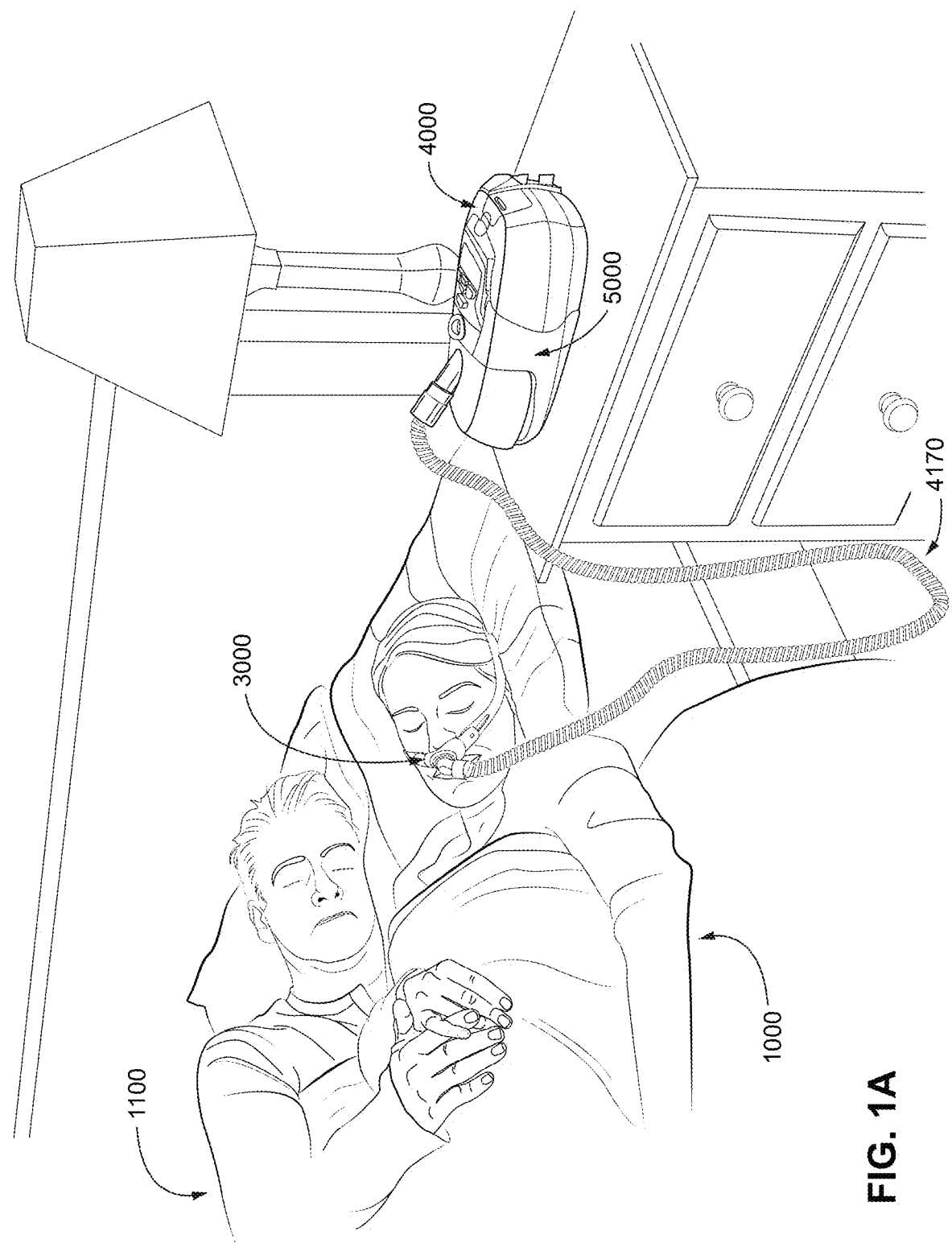
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
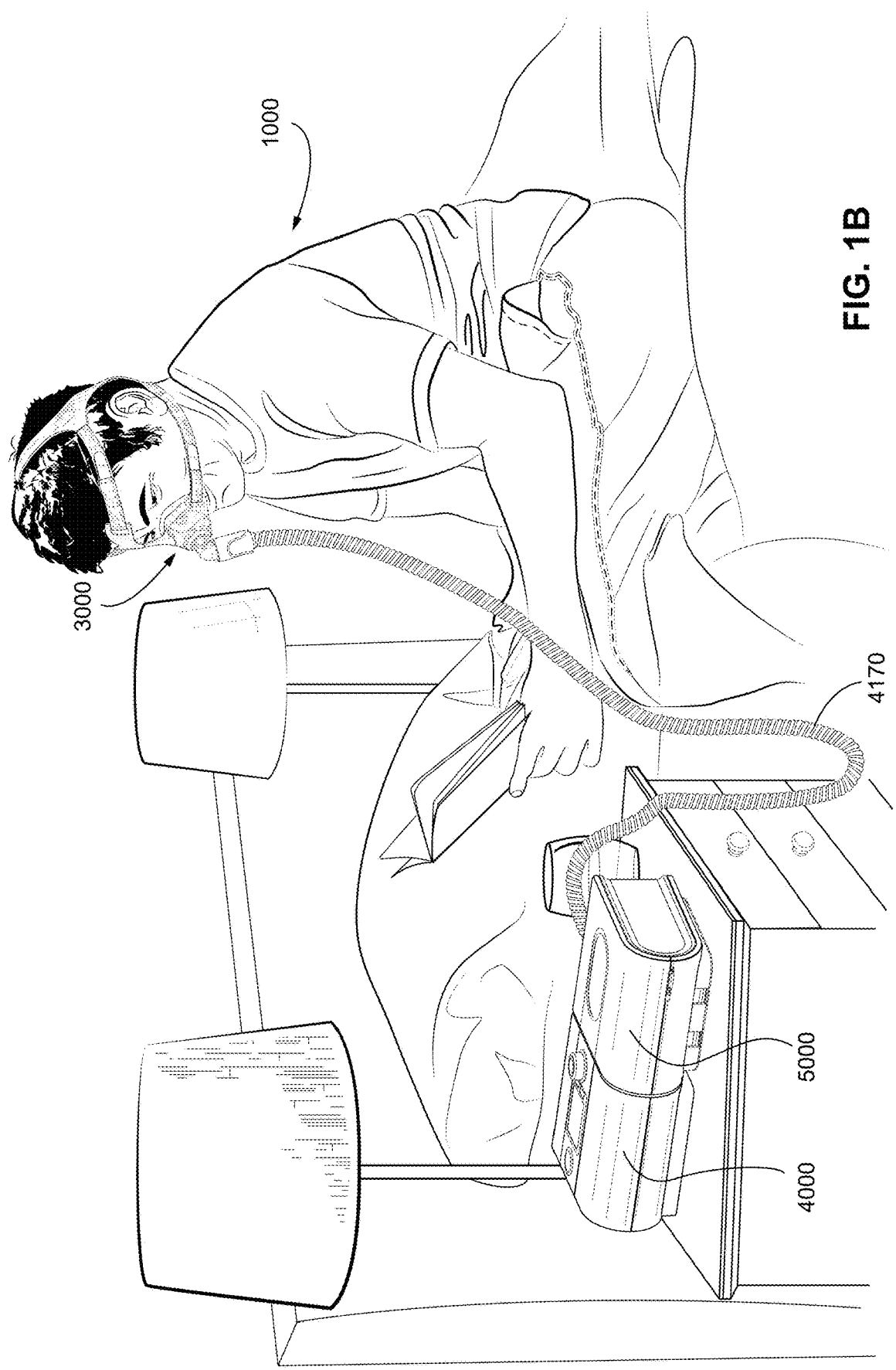
Figure 1C:
Figure 2A:
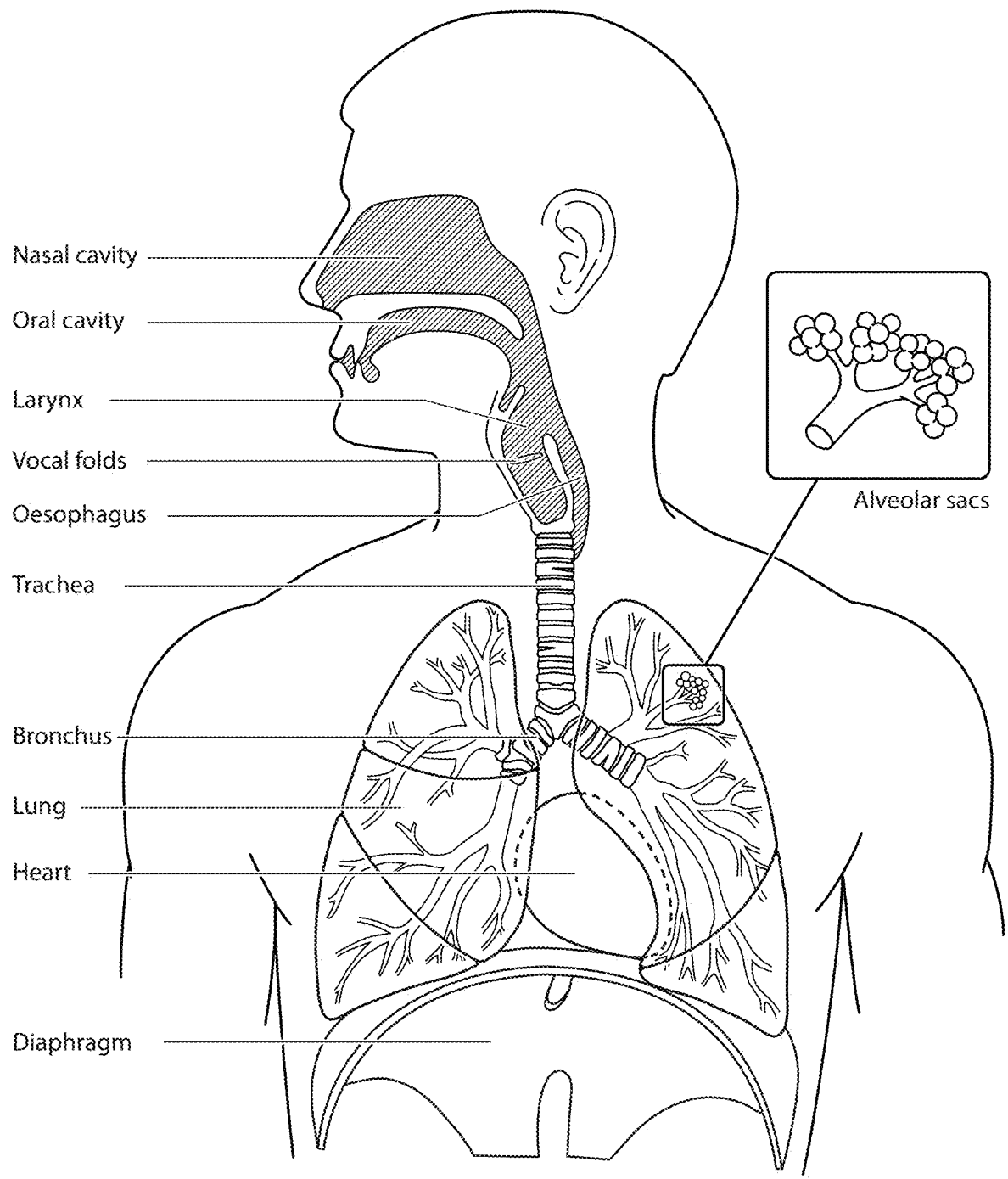

FIG. 2A shows an overview of a human respiratory system including the nasal and oral cavities, the larynx, vocal folds, oesophagus, trachea, bronchus, lung, alveolar sacs, heart and diaphragm.

Figure 2B:
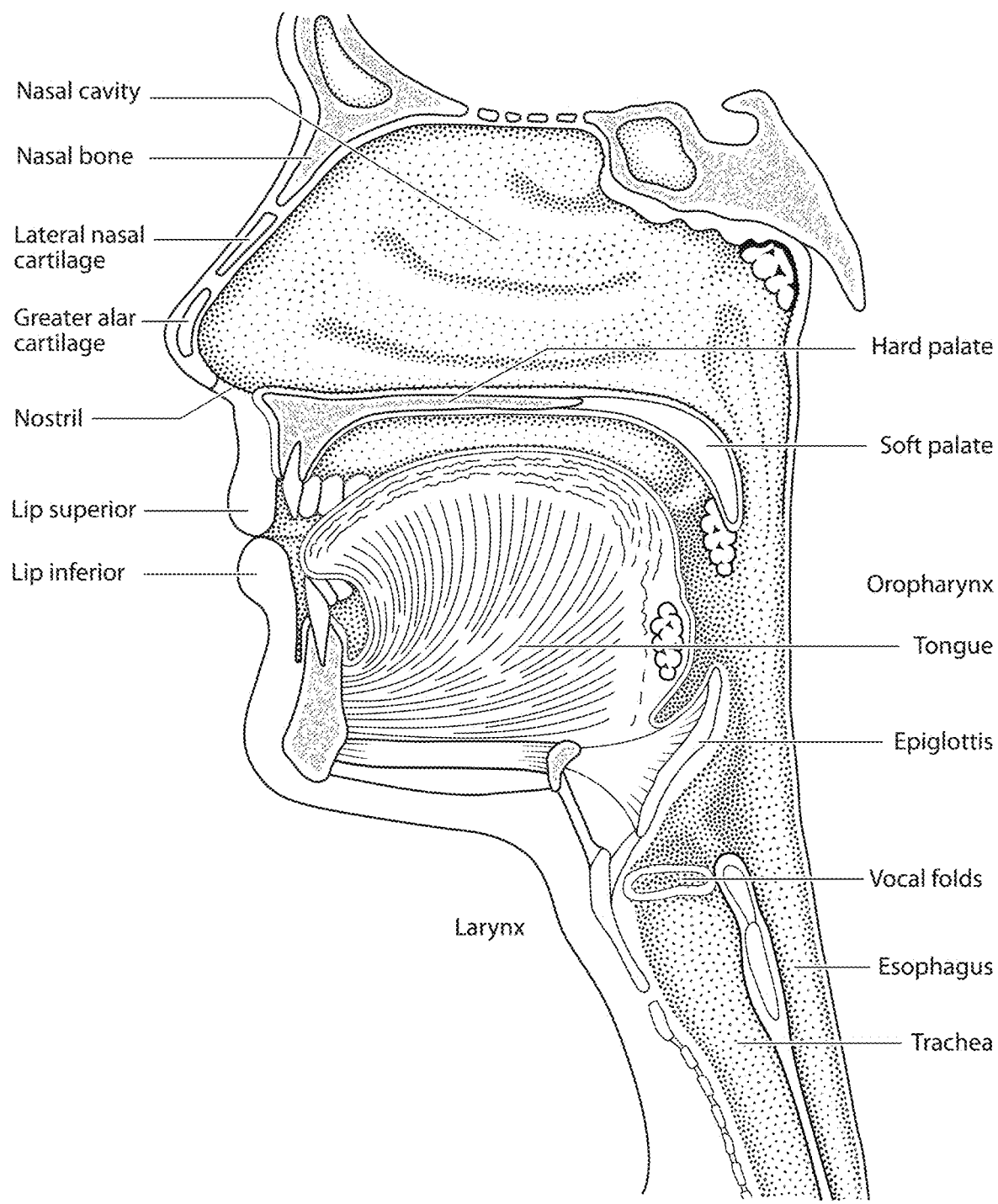

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3A:
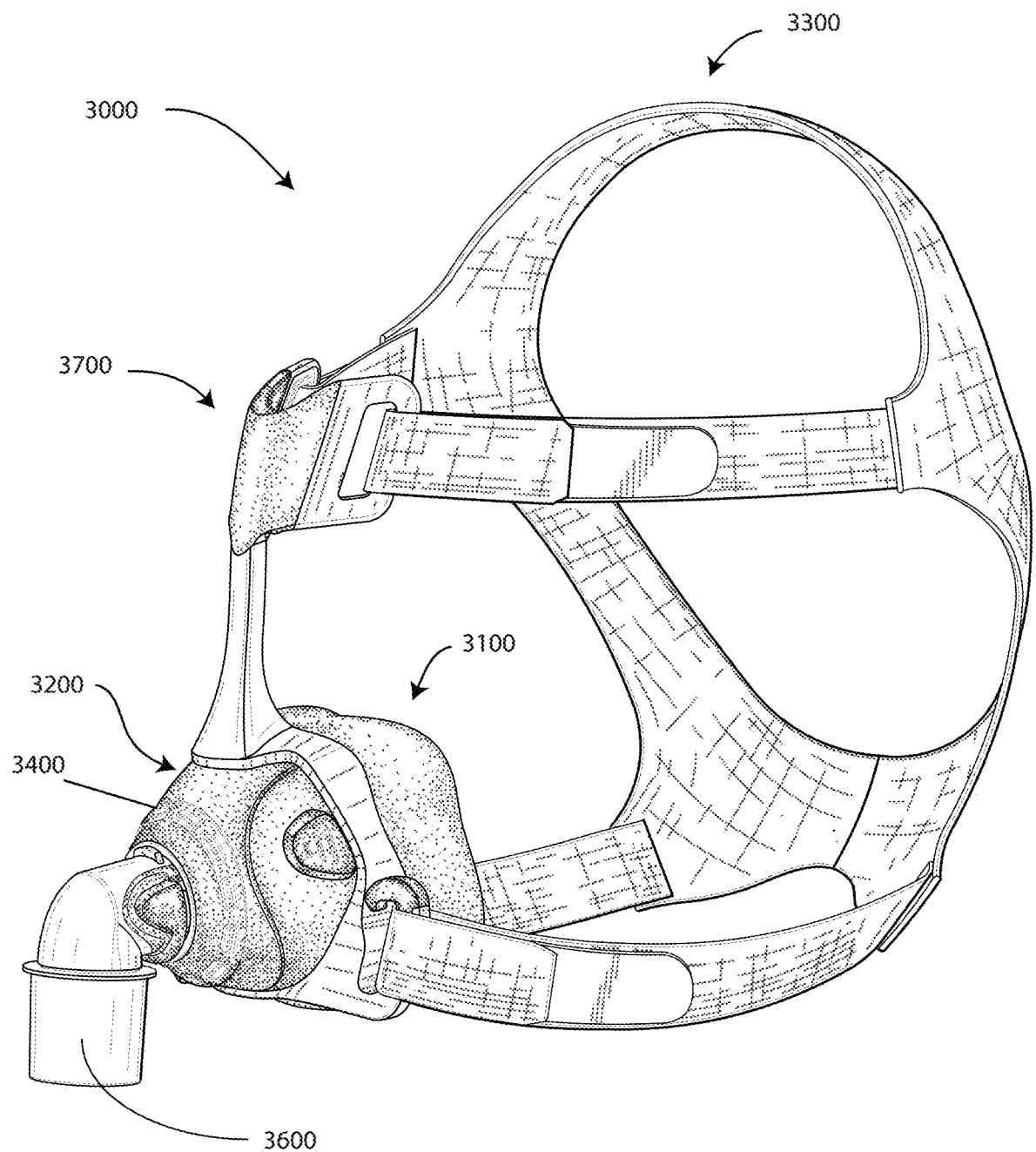

FIG. 3A shows a patient interface in the form of a nasal mask in accordance with one form of the present technology.

4.4 RPT Device

Figure 4A:
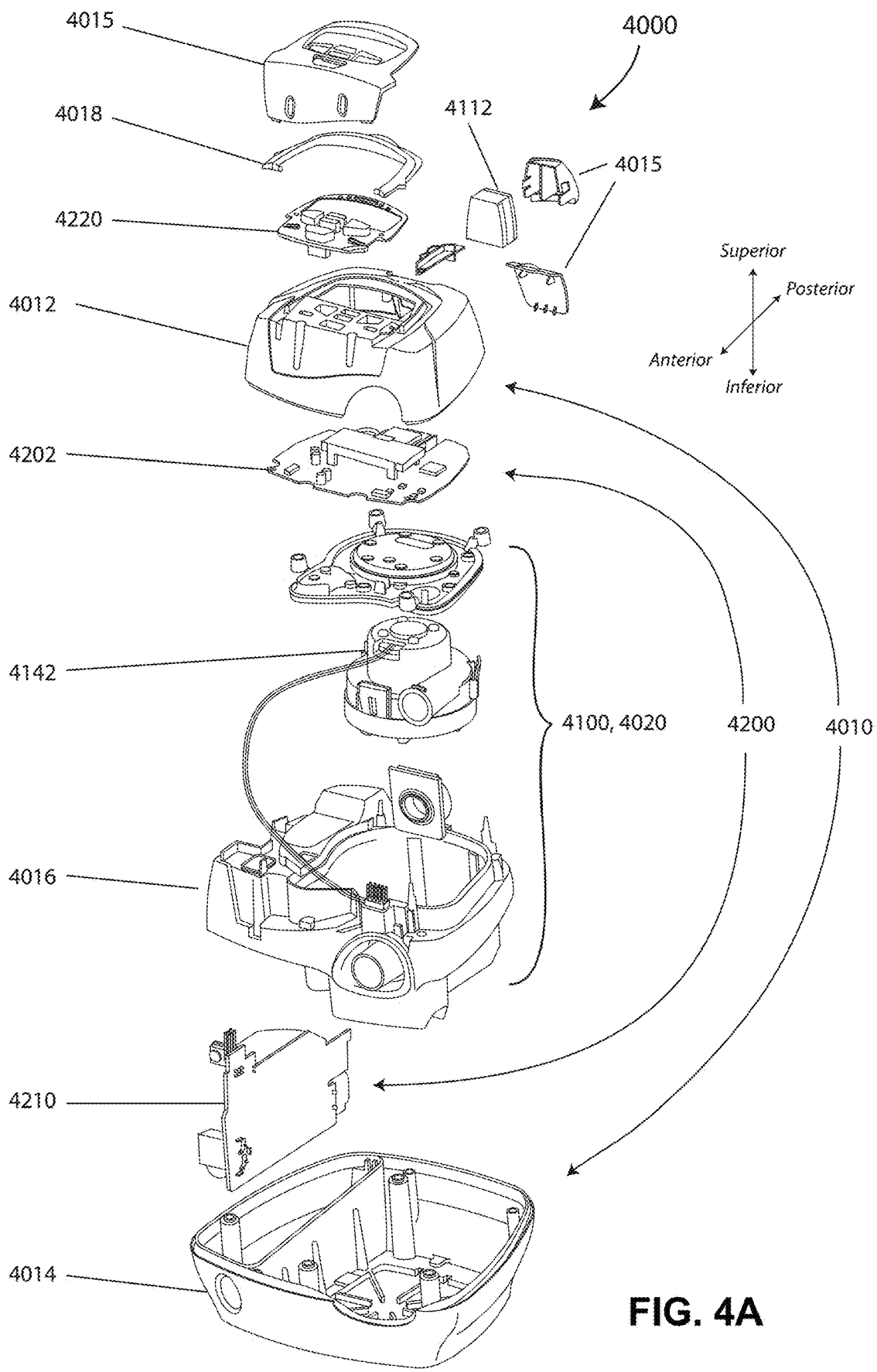

FIG. 4A shows an RPT device in accordance with one form of the present technology.

Figure 4B:
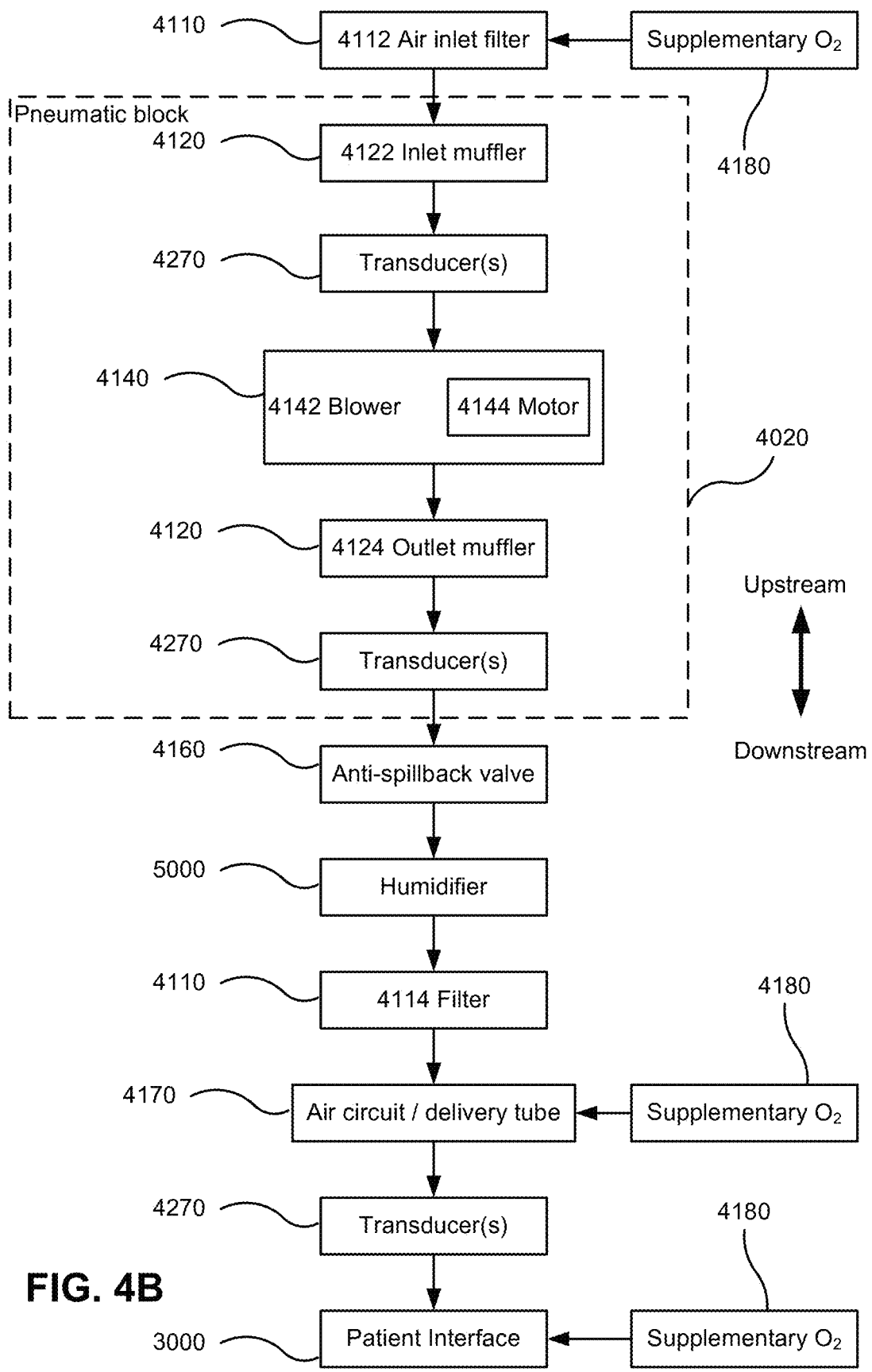

FIG. 4B is a schematic diagram of the pneumatic path of an RPT device in accordance with one form of the present technology. The directions of upstream and downstream are indicated.

Figure 4C:
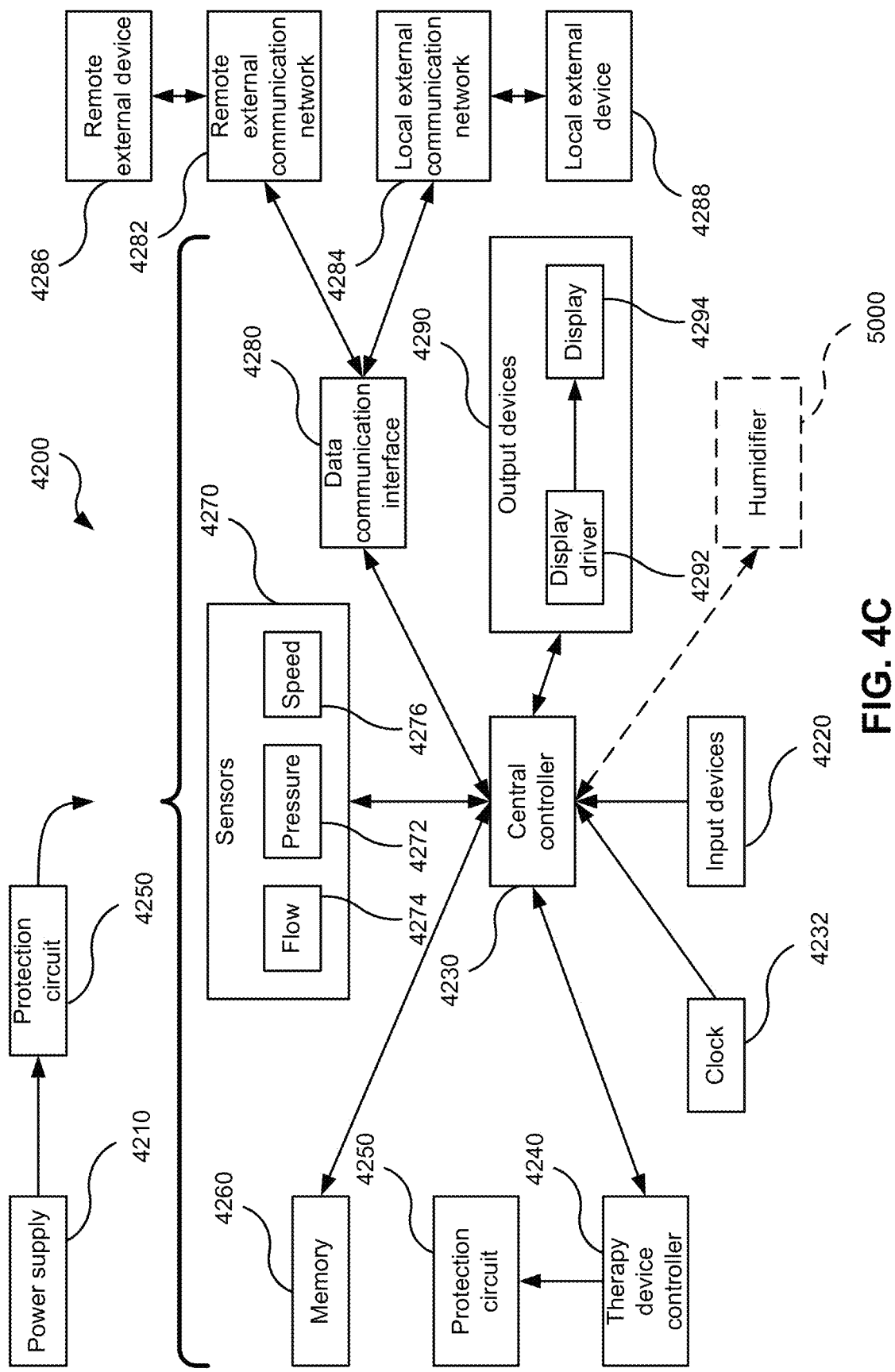

FIG. 4C is a schematic diagram of the electrical components of an RPT device in accordance with one form of the present technology.

4.5 Breathing Waveforms

Figure 5:
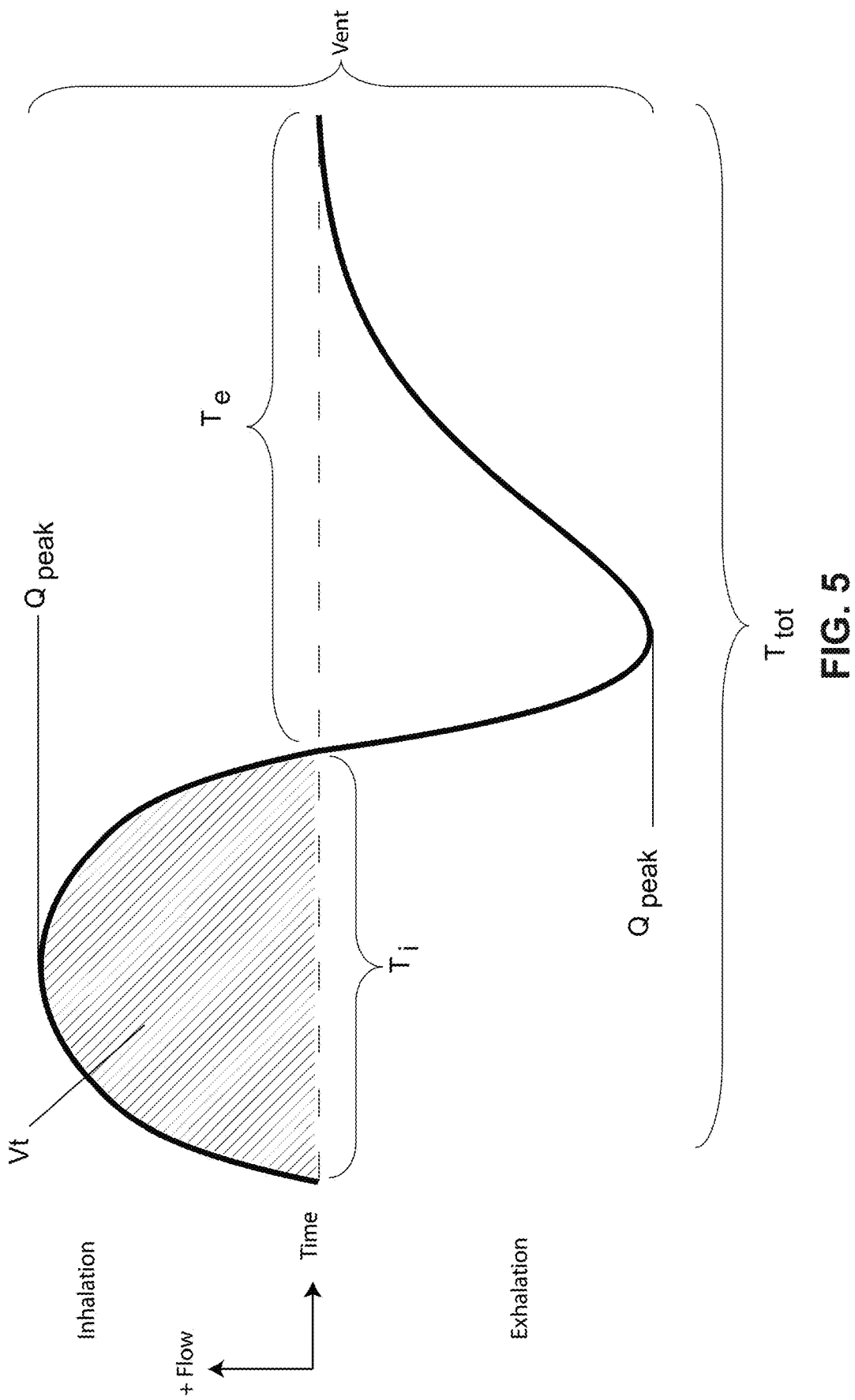

FIG. 5 shows a model typical breath waveform of a person while sleeping. The horizontal axis is time, and the vertical axis is respiratory flow. While the values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

4.6 Humidifier

Figure 6:
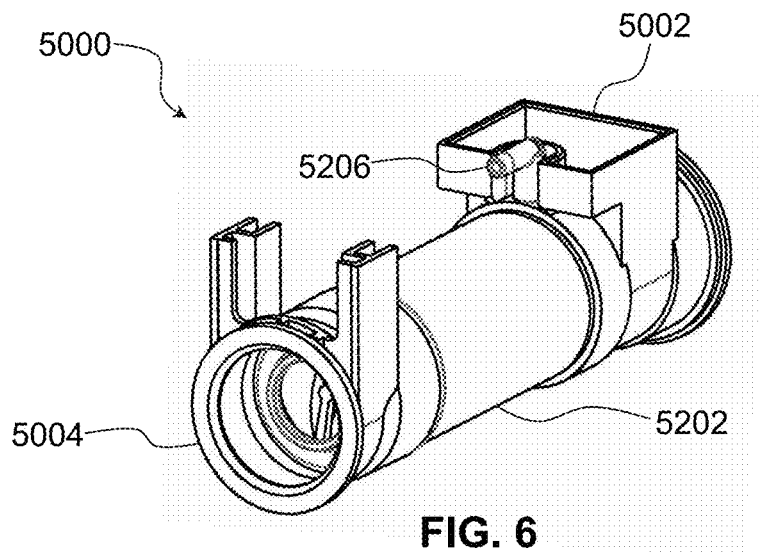

FIG. 6 shows a perspective view of a humidifier 5000 according to one aspect of the present technology.

Figure 7:
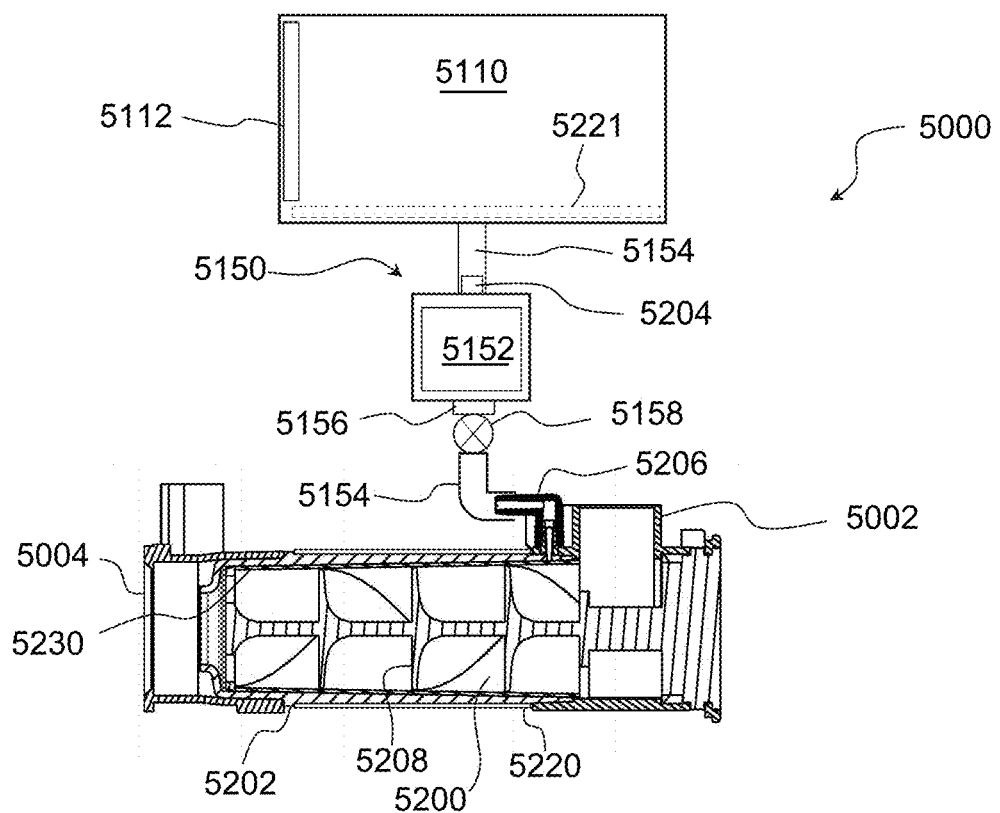

FIG. 7 shows a schematic view of the humidifier of FIG. 6 further comprising a water delivery mechanism 5150 and a reservoir 5110.

Figure 8A:
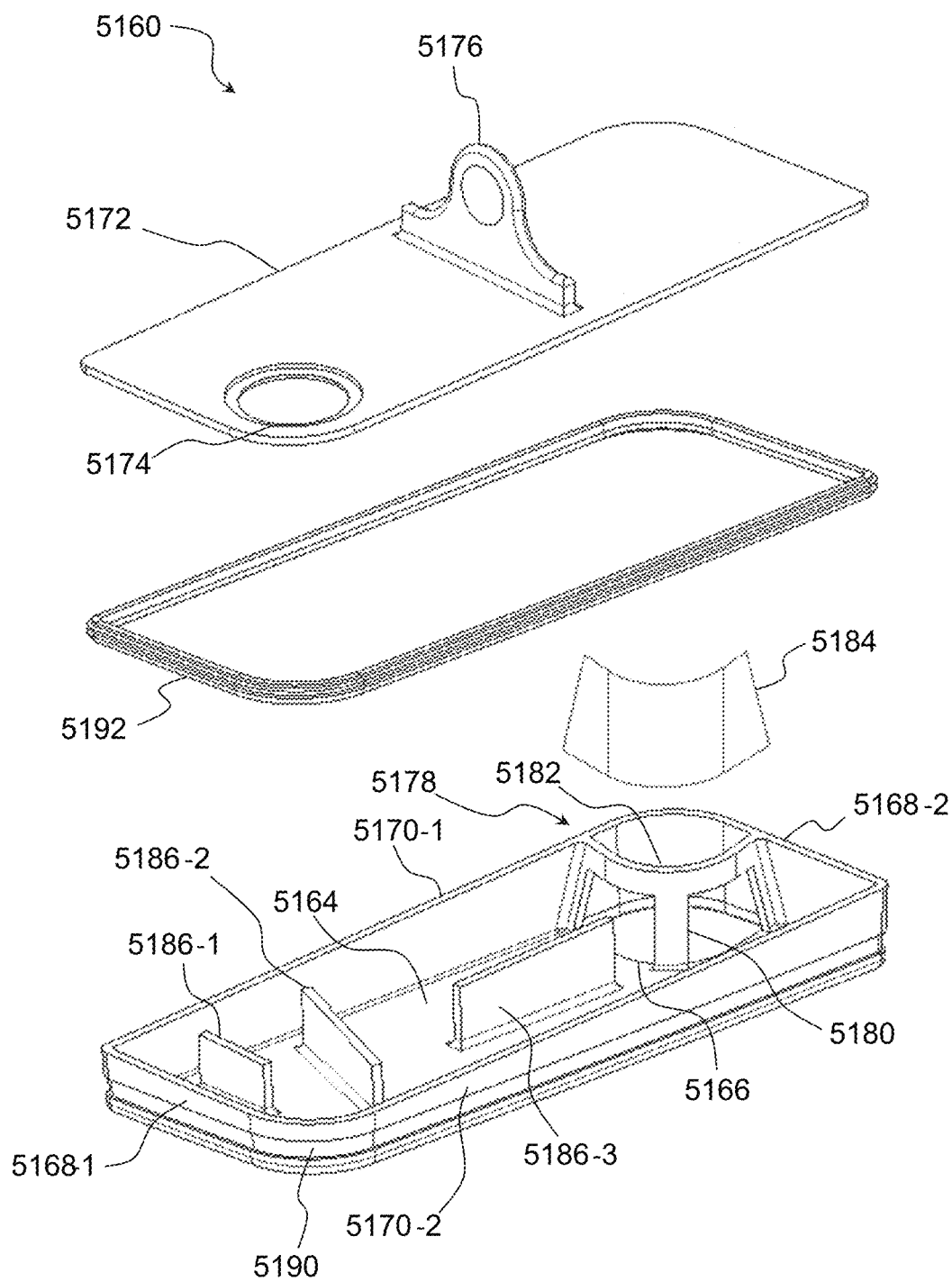

FIG. 8A shows a perspective exploded view of a deioniser cartridge 5160 for use with the humidifier in accordance with one form of the present technology.

Figure 8B:
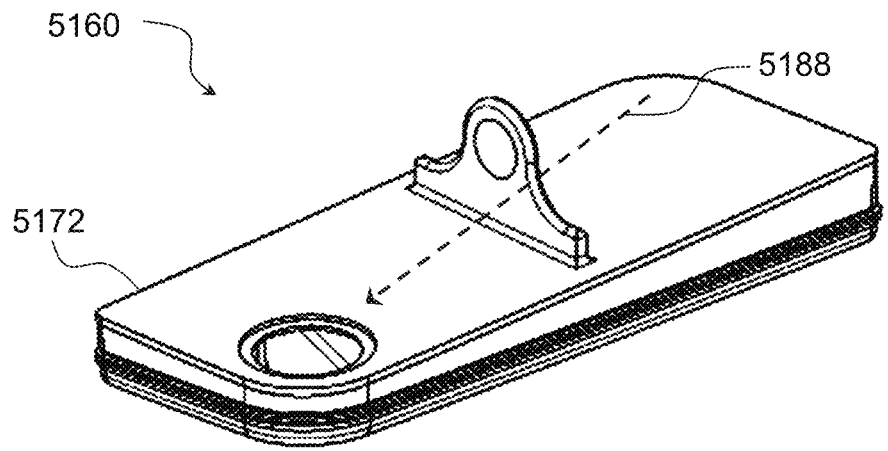

FIG. 8B shows a perspective view of the deioniser cartridge 5160.

Figure 8C:
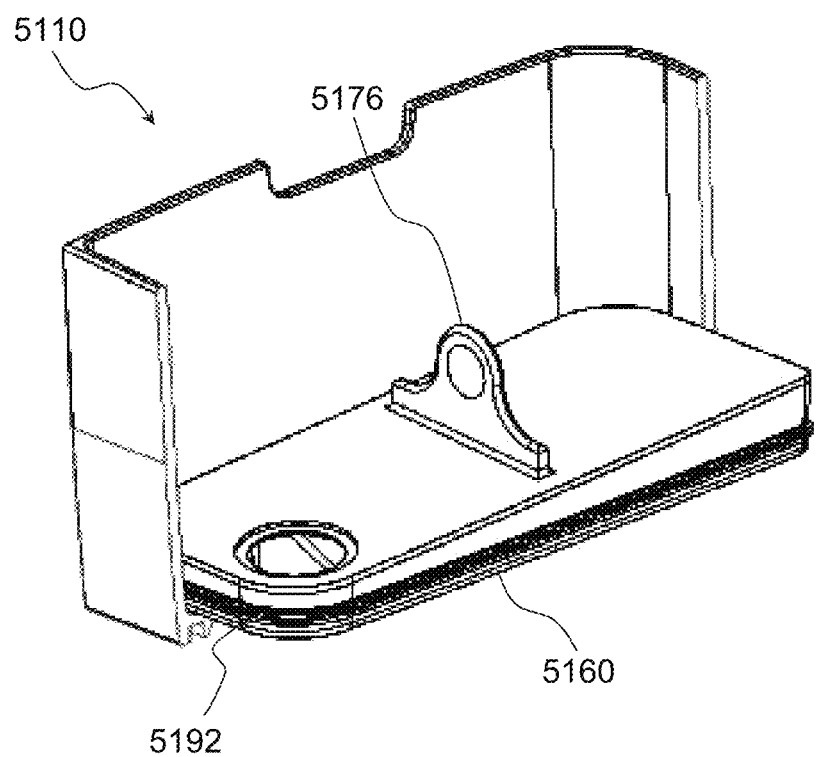

FIG. 8C shows a perspective view of the deioniser cartridge 5160 in place in the reservoir 5110.

Figure 9:
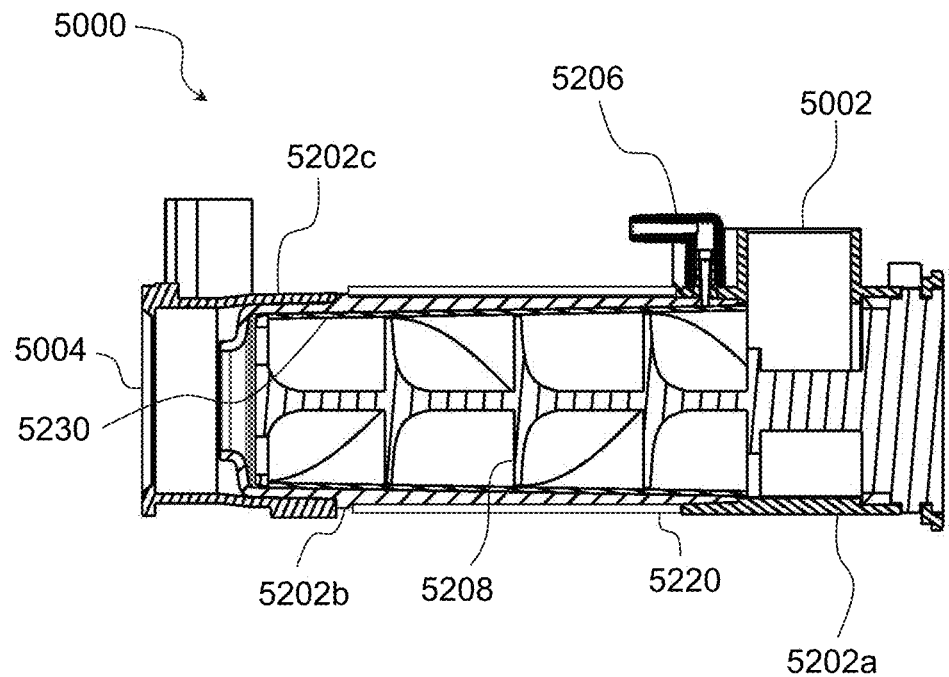

FIG. 9 shows a cross-section view in elevation of the humidifier of FIG. 6.

Figure 10:
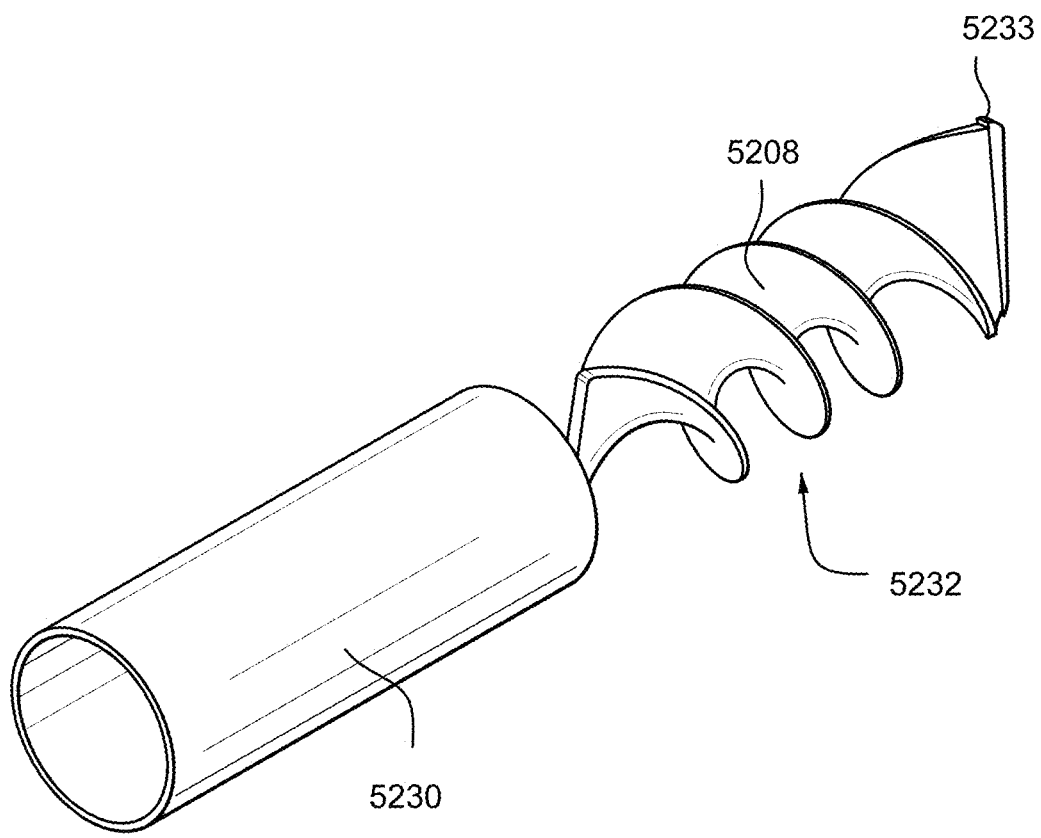

FIG. 10 shows an exploded perspective view of a portion of the humidifier 5000 of FIG. 6 showing a humidifier wick 5230 and a wick frame 5232.

Figure 11A:
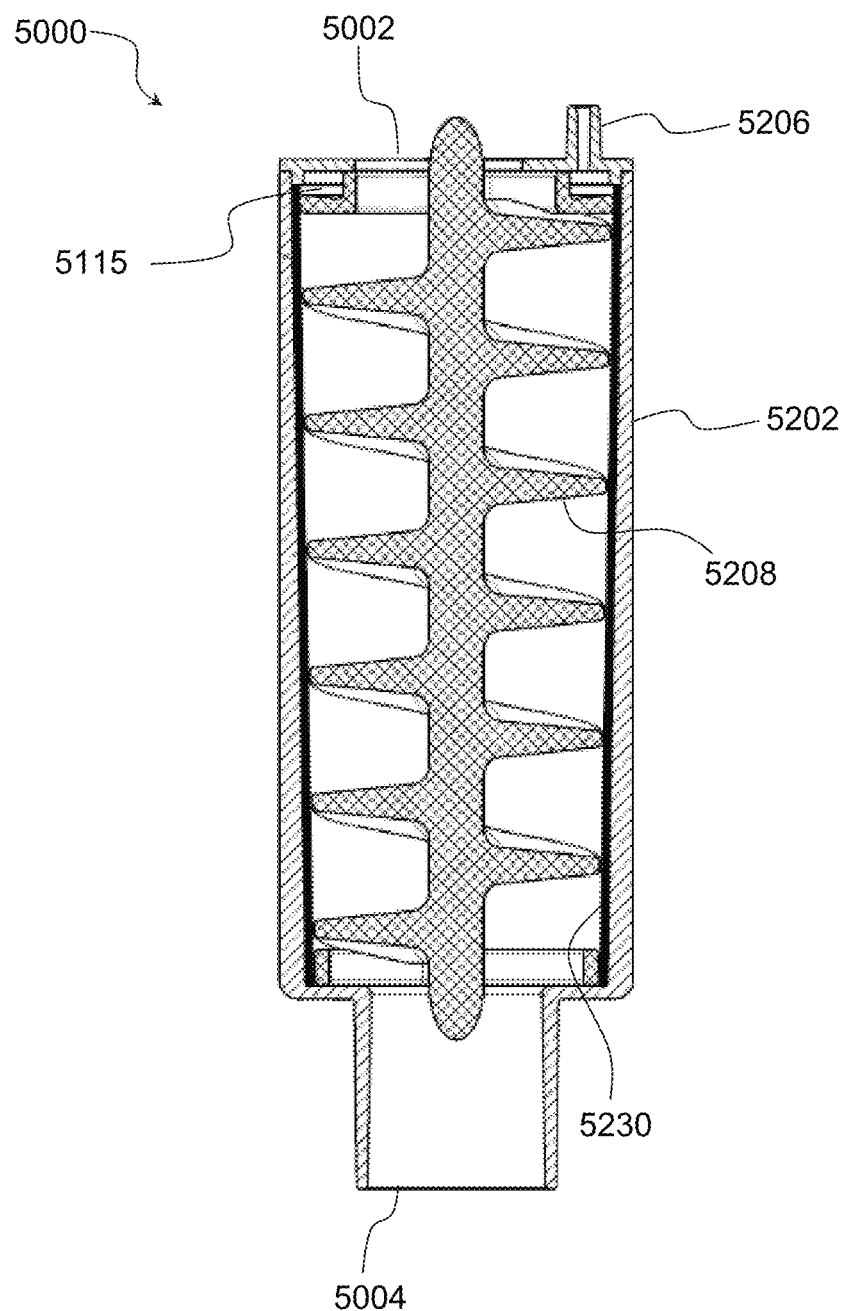

FIG. 11A shows a cross-section view of a humidifier in a vertical orientation according to an aspect of the present technology.

Figure 11B:
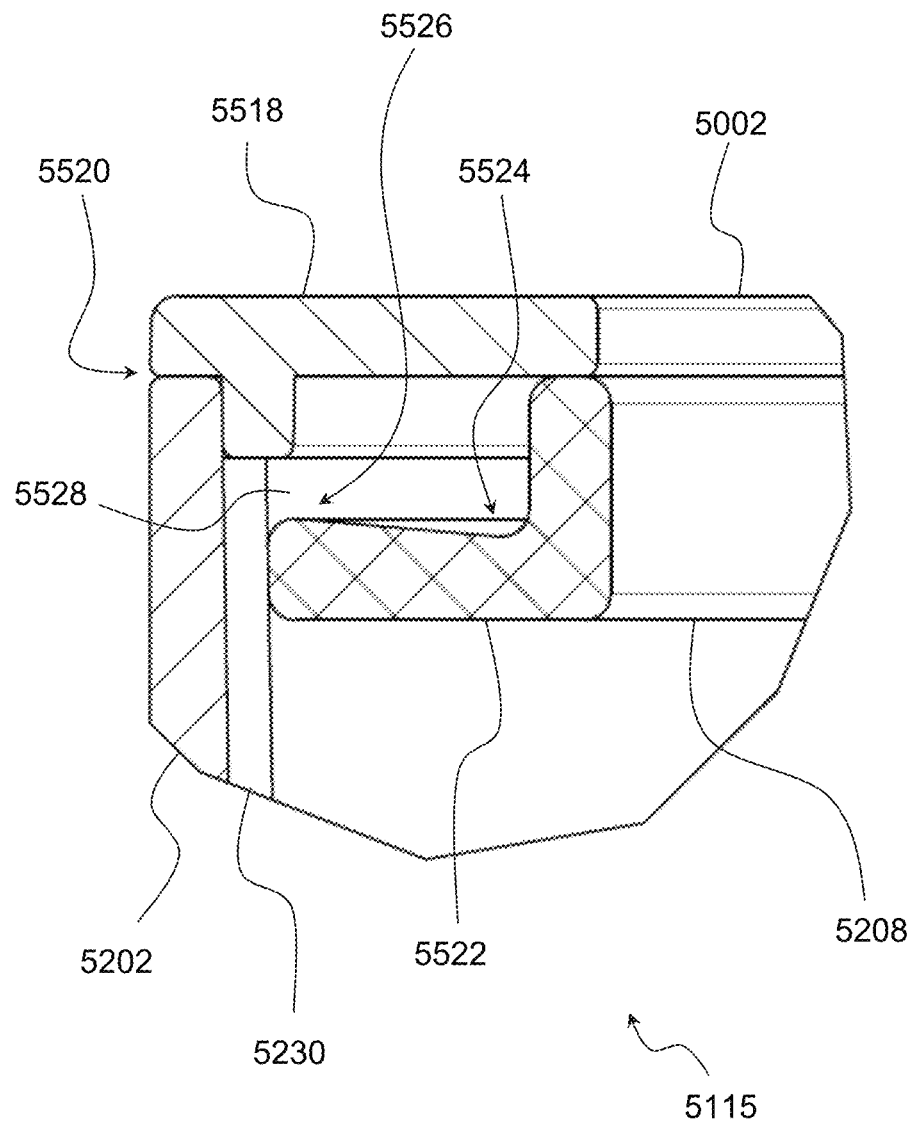

FIG. 11B shows a cross-section view of a pre-delivery chamber 5115 of the humidifier according to an aspect of the present technology.

Figure 12:
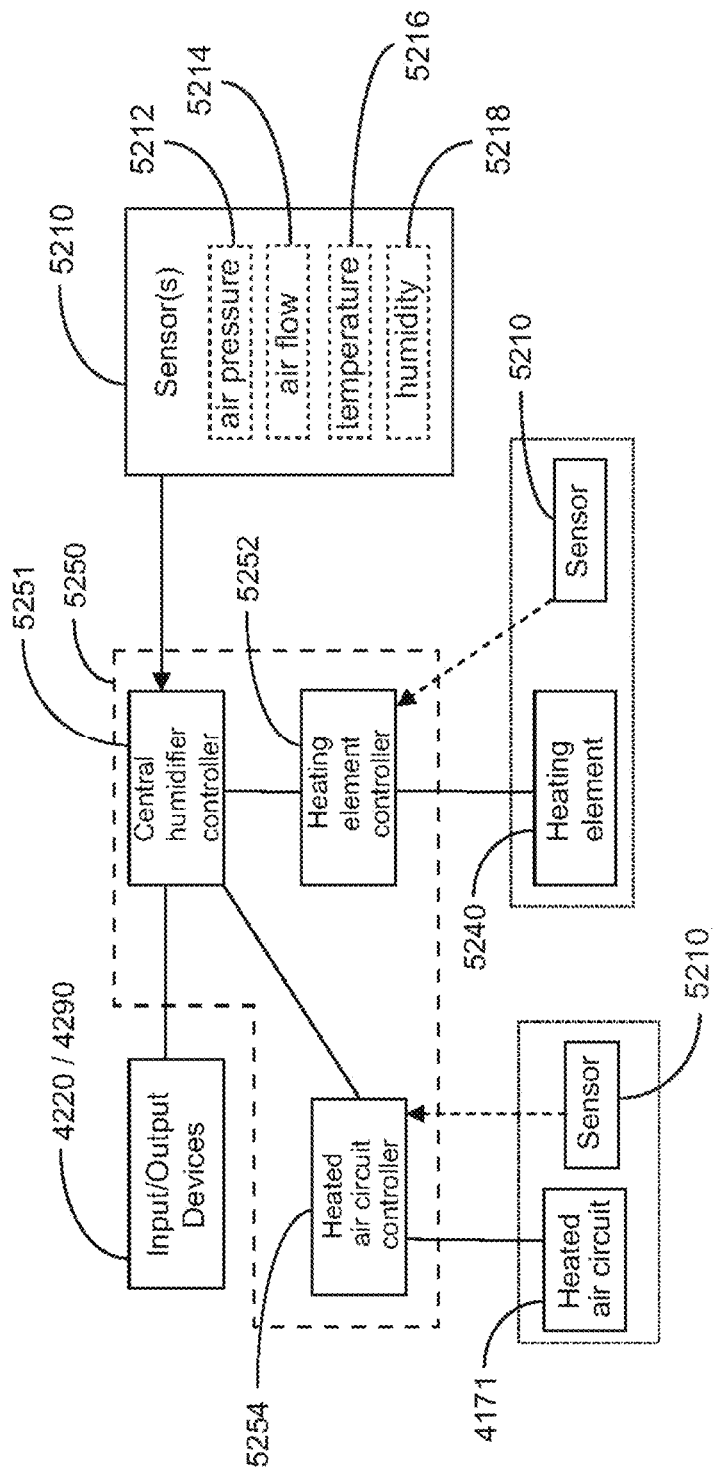

FIG. 12 shows a schematic of a humidifier in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

In one form the patient interface 3000 includes at least one decoupling structure, for example, a swivel or a ball and socket.

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with an aspect of the present technology is a conduit or a tube constructed and arranged to allow, in use, a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Humidifier

5.5.1 Humidifier Overview

In one form of the present technology there is provided a humidifier 5000 (e.g. as shown in FIG. 6) to change the absolute humidity of air or gas for delivery to a patient relative to ambient air. Typically, the humidifier 5000 is used to increase a moisture content, or absolute humidity, of the flow of air (relative to ambient air) before delivery to the patient's airways.

The humidifier 5000 may comprise a humidifier inlet 5002 to receive a flow of air, and a humidifier outlet 5004 to deliver a humidified flow of air.

5.5.2 Humidifier Components

5.5.2.1 Water Reservoir

According to one arrangement, the humidifier 5000 may comprise, or be coupled to, a water reservoir 5110 as shown in FIG. 7. The water reservoir 5110 may be configured to hold, or retain, a predetermined maximum volume of liquid (e.g. water or other suitable liquids, such as medications, scenting agents or a mixture containing such additives) to be evaporated for humidification of the flow of air.

In one form, the reservoir 5110 may be configured to hold several hundred millilitres of water, for use during at least the length of the patient's sleep in a day. However, in other forms, other sizes such as a smaller reservoir for a portable, travel-friendly system or a larger reservoir for a hospital system may be also suitable. Yet further, a reservoir 5110 may be replaced by, or connected to, a water supply.

According to some arrangements, the reservoir 5110 may comprise, or be coupled to, a water volume detector 5112 by which the amount of water in the reservoir 5110 may be determined. The water volume detector 5112 may determine the volume of water based on one or more of a presence, weight, optical property, ultrasonic property or a head (height) of the water of the reservoir 5110. Any of the mechanisms or methods such as those described in the International Patent Application Publication No. WO 2015/058255 may also be suitable for use with the present technology, the entire contents of which is incorporated herewithin by cross-reference.

In some forms, the reservoir 5110 may be configured to heat the water prior to the water entering the humidification chamber 5200, for example by comprising, or being coupled to, a reservoir heating element 5221 as shown in FIG. 7.

In one form, the reservoir 5110 may comprise a plurality of liquid chambers, for example each containing a different fluid. In one example, a first chamber may comprise a volume of water while a second chamber may comprise medication (e.g. dissolved in liquid), or scenting agent (e.g. tea tree oils). The liquids from the plurality of liquid chambers may be mixed prior to or during delivery to the humidifier or within the humidifier 5000. Alternatively, the humidifier may deliver only one of the liquids from the plurality of liquid chambers at any one time.

5.5.2.2 Water Delivery Mechanism

According to one aspect of the present technology, the humidifier 5000 may comprise a water delivery mechanism 5150 configured to deliver a flow of water from the reservoir 5110 to a humidification chamber 5200 (see FIG. 7). The water delivery mechanism 5150 may comprise a water pump 5152 and a water delivery conduit 5154, and may be in fluid communication with a water feed inlet 5206 to deliver the flow of water to the humidification chamber 5200. The water delivery mechanism 5150 may additionally or alternatively comprise one or more of hydraulic channels, capillary channels or holes. The water delivery mechanism 5150, in some forms of the present technology, may further comprise a valve (e.g. water check valve 5158) for controlling delivery of water from the reservoir 5110 to the humidification chamber 5200. The water delivery mechanism 5150 may be configured to allow or prevent delivery of water through to the water feed inlet 5206 from the reservoir 5110. For example, the valve may be configured to controllably allow a flow of water to travel from the reservoir 5110 to the humidification chamber 5200, such as only when the humidifier 5000 is in operation.

The humidification chamber 5200 may comprise a water retention feature such as a humidifier wick 5230, which receives the flow of water from the water delivery mechanism 5150. In some forms, the humidifier 5000 may comprise a plurality of water delivery mechanisms 5150 and/or a plurality of water feed inlets 5206 in order to better control a distribution of water in the humidifier wick 5230 (e.g. more uniformly).

The water flow rate(s) that the humidifier 5000 is configured to provide may vary according to factors such as the configuration of the humidifier 5000 and a range of expected operating conditions such as ambient conditions (e.g. ambient temperature/humidity), humidifier operating parameters (e.g. maximum heat output of the heating element 5220, maximum water capacity of the humidifier wick 5230) and/or therapy conditions (e.g. therapy pressure, air flow rate, patient comfort/preference). For example, a change in therapy pressure only may cause a change in the water flow rate, such as due to a response by the humidifier controller 5550, or due to a property of the water delivery mechanism 5150.

In one form, the range of water flow rates able to be provided by the humidifier 5000 may be between 0 ml/min and 2 ml/min, between 0 ml/min and 1 ml/min, or between 0 ml/min and 0.5 ml/min. In one form, the humidifier 5000 may be configured to provide one of a number of discrete water flow rates at any given time, for example 0.0 ml/min, 0.2 ml/min, 0.4 ml/min, 0.6 ml/min, or 0.8 ml/min, where the limits of water flow rates able to be provided are 0.0 ml/min and 0.8 ml/min. In other forms, the humidifier 5000 may be configured to provide any water flow rate between an upper limit and a lower limit by providing an analogue control of the flow rate, i.e., the water flow rate may be infinitely adjustable within the upper limit and the lower limit. The upper limit and lower limit of water flow rates may vary according to aspects of a humidifier, such as one or more of: maximum humidity output, maximum flow rate of air through the humidifier, a size of the humidifier, and properties of the wick (e.g. exposed surface area and/or water capacity). In cases where at least one liquid other than (or additional to) water is used, the flow rates for each liquid may vary accordingly. The flow rate at a particular time during operation of the humidifier 5000 may also depend on the set of operating conditions at the particular time. For example, a typical value with an air flow rate of 35 l/min and desired added humidity of 15 mg/l requires a water flow of 0.5 ml/min.

It is noted that air flow rates in respiratory therapy may vary over a short term, for example, due to a breath cycle of a patient. However, in some examples, such as determining an appropriate water flow rate based on an air flow rate, a humidifier algorithm may utilise an air flow rate where effects of such variation is removed, or reduced. Thus, the air flow rate may be low-pass filtered, or be based on a continuous average, wherein the time constant (e.g. in filtering, or an average time) would be sufficiently long to reduce or remove the effects of in-breath variations.

A pressure of the flow of air (also known as air pressure) in an RPT device and its pneumatic path downstream thereof may vary during therapy, for example between 4 and 30 cmH$_2$O. Thus, the water pump 5152 may be configured to deliver a consistent water flow rate across various air pressures in the humidifier 5000. The water flow rate provided by the water pump 5152 may be independent from (i.e. not be affected by) the air pressure in the humidifier 5000. Such a water pump 5152 would be advantageous in that the air pressure may be varied independently of the amount of humidification provided thereto for improved controllability of the therapy system.

In one form, the water pump 5152 may be a positive displacement type pump. In another form, many other types of pumps such as a metered pump, a peristaltic pump, a gravity-fed pump, or a pumps utilising blower pressure may be suitable to be used in the water delivery mechanism 5150.

An elevated reservoir (not shown) such as a drip bag may also be suitable, and may act as a type of gravity fed pump to deliver water.

In some forms, where a water flow rate through the water pump 5152 may be affected by the air pressure, the flow rate through the water pump 5152 may be compensated accordingly. For instance, as shown in FIG. 7, the water delivery mechanism 5150 may additionally comprise one or more of a metering mechanism 5156 to measure the water flow rate and/or a water check valve 5158 to control the water flow rate through the water pump 5152. Alternatively, the humidifier controller 5550 may be used to compensate for the effects of any changes to the air pressure, by controlling the water pump 5152 according to the air pressure. A measure of the air pressure may be received by the humidifier controller 5550 as an input to enable such control. In some forms, the humidifier controller 5550 may be used to compensate for the effects of any changes to the air flow rate (e.g. due to a change in leak), by controlling the water flow rate through the water delivery mechanism 5150.

In another arrangement (not shown), a water pump 5152 may be configured to pump water by utilising a pressure such as that generated by the RPT device 4000. The pressure may then be used to draw water from the reservoir 5110 into the humidification chamber 5200. The water flow rate in such an arrangement may be a function of the air flow rate, and thus the humidifier 5000 in this arrangement may further comprise a control valve to regulate the water flow rate.

The humidifier 5000 may in some forms comprise a fault detection mechanism to detect conditions such as blockages in the water delivery mechanism 5150 or a shortage of water in the reservoir 5110, as will be described in further detail below. For example, a blockage in a positive displacement pump may cause its motor to stall, causing the pump to stop. Furthermore, the humidifier 5000 may be configured to detect accumulation of precipitates and/or contamination, such as in the wick 5230, as precipitants or contaminants may adversely affect performance of the humidifier 5000, such as the wick by reducing the ability of the wick 5230 to absorb water.

In one form of the present technology, the water feed inlet 5206 may be in fluid communication with the water delivery mechanism 5150 (as shown in FIG. 7) to deliver water to the humidifier wick 5230. In some cases, the humidifier 5000 may comprise a water filter 5204 configured to reduce ingress of foreign matter into the humidification chamber 5200 and/or the wick 5230 through the flow of water. The water filter 5204 may be located at or near an outlet of the reservoir 5110 (as shown in FIG. 7) or upstream (prior to) the water feed inlet 5206. The water filter 5204, or parts thereof, may be configured to be replaceable or cleanable.

5.5.2.2.1 Deioniser

In one form of the present technology, the humidifier may comprise a deioniser configured to soften the water—i.e. remove at least a portion of scale forming ions—prior to delivery of the water to the water feed inlet 5206. Thus, the deioniser may be positioned upstream of the water feed inlet 5206 relative to the flow of water.

In some forms the water filter 5204 may comprise a deioniser, while in other forms the deioniser may be additional to, or in place of, the water filter 5204.

In one form of the present technology, the deioniser may comprise an ion exchange resin as the medium by which deionisation is achieved. As an example, a suitable ion exchange resin may include the CA-10 ion exchange resin produced by CARBOCHEM.

In one form of the present technology, the deionisation medium may include more than one type of ion exchange resin. As an example, the deionisation medium may include a first type of resin configured to remove positively charged ions (cations) and a second type of resin configured to remove negatively charged ions (anions). In one form, the first and second types of resin may be provided in separate stages. In one form, the first and second types of resin may be mixed in a single stage.

It is envisaged that the relatively low flow rates intended for use in forms of the present technology may allow for the use of such ion exchange resins.

In one form of the present technology, the deioniser may comprise a deioniser cartridge 5160 as shown in FIG. 8A. The deioniser cartridge 5160 may comprise a base portion 5164 having a cartridge outlet 5166. First end wall 5168-1 and second end wall 5168-2 may extend from distal ends of the base portion 5164, joined by first side wall 5170-1 and second side wall 5170-2.

A lid 5172 may be provided to seal against the walls 5168-1, 5168-2, 5170-1, and 5170-2. In one form the lid 5172 may be releasably attached in place, although in another form it may be permanently secured. A cartridge inlet 5174 may be provided in the lid 5172 toward a corner distal from the cartridge outlet 5166. In one form of the present technology, the deioniser cartridge 5160 may comprise a handle 5176 for grasping by a user to remove or replace the deioniser cartridge 5160 in the reservoir 5110.

In one form of the present technology, the deioniser cartridge 5160 may comprise a filter frame 5178 at the cartridge outlet 5166, comprising frame legs 5180 extending from the base portion 5164, and an upper frame member 5182 extending between the second end wall 5168-2 and first side wall 5170-1 and frame legs 5180. The filter frame 5178 may have a non-zero draft angle to allow for manufacture by moulding as a unitary part with the base portion 5164. In an exemplary embodiment, a filtration member in the form of polymer mesh 5184 may be secured to the filter frame 5178, for example by welding. The mesh 5184 may restrict the escape of ion exchange medium, for example ion exchange resin(s), from the cartridge 5160.

In one form of the present technology, the deioniser cartridge 5160 may comprise a plurality of baffles extending from the base portion 5164, for example a first baffle 5186-1, a second baffle 5186-2, and a third baffle 5186-3. The baffles 5186-1, 5186-2, and 5186-3 may be used to distribute water flow through the cartridge 5160 between the inlet 5174 and the outlet 5166 in order to achieve load levelling on the resin.

In one form of the present technology, the height of the second end wall 5168-2 may be greater than the height of the first end wall 5168-1, with the first side wall 5170-1 and second side wall 5170-2 increasing in height between the first end wall 5168-1 and the second end wall 5168-2. The first end wall 5168-1 may also decrease in height toward the second side wall 5170-2. Referring to FIG. 8B, the resulting draft along the lid 5172 assists in encouraging the draining of water towards the inlet 5174, as indicated by dashed arrow 5188. While not illustrated, it should be appreciated that in one form of the present technology a draft may be provided in the base portion 5164 to encourage draining between the inlet 5174 and outlet 5166.

Returning to FIG. 8A, in one form the deioniser cartridge 5160 may comprise a seal recess 5190 around the exterior of the first end wall 5168-1, second end wall 5168-2, first side wall 5170-1 and second side wall 5170-2, configured to receive a seal 5192. When seated in the reservoir 5110, as shown in FIG. 8C, the seal 5192 prevents flow of water around the sides of the deioniser cartridge 5160. This ensures exposure of the water to the deionisation medium, for example ion exchange resin(s), within the deioniser cartridge 5160 before exiting the cartridge outlet 5166.

5.5.2.2.2 Pasteurisation

In one form of the present technology, the humidifier 5000 may be configured to pasteurise water to be delivered to the humidifier wick 5230.

In one form of the present technology, the humidifier 5000 may be configured to heat the water delivery conduit 5154, thereby potentially pasteurising the conduit itself in addition to the water passing through it.

In one form of the present technology a dedicated heating element may be provided for heating of the water delivery conduit 5154. In another form, the water delivery conduit 5154 may be thermally coupled to the heating element 5220 of the humidification chamber 5200—for example, disposed around the exterior of the humidification chamber 5200 against the heating element 5220.

It is envisaged that the requisite temperature levels over time for pasteurisation may necessitate a cleaning mode, in which normal operation of the humidifier 5000 is suspended. In one form, such a cleaning mode may be initiated periodically, or on detection of conditions which indicate that the device is not in demand and it is safe to initiate the cleaning mode.

In one form of the present technology the cleaning mode may be initiated on insertion of a component into the humidifier. For example, the component may be a sealing member configured to seal an outlet of the humidifier so as to ensure that the humidifier is not inadvertently used during the cleaning mode.

In another form initiation of the cleaning mode may be on receiving a user input.

5.5.2.3 Humidification Chamber

According to one aspect, the humidifier 5000 may comprise a humidification chamber 5200, in which moisture is added to the flow of air, thus increasing the absolute humidity, prior to being delivered to the patient 1000.

In one form the humidification chamber 5200 may be as described in any one of the following patents or patent applications, the contents of which are incorporated herein by reference in their entirety: International Patent Application Publication No. WO 2015/135040 and International Patent Application Publication No. WO 2016/139645.

In one form, a cross-section of which is shown in FIG. 9, the humidification chamber 5200 may comprise a humidifier wick 5230, a water feed inlet 5206 and a heating element 5220. The humidification chamber 5200 may be in fluid communication with, and receives water from, the reservoir 5110 through the water feed inlet 5206.

In the form illustrated, the humidification chamber 5200 may comprise a chamber housing 5202 configured to define and protect an interior of the humidification chamber 5200, such as any components therein. The chamber housing 5202 may comprise a plurality of portions such as an inlet portion 5202a, central portion 5202b and outlet portion 5202c that are coupled together. The inlet portion 5202a may comprise the humidifier inlet 5002 and the outlet portion 5202c may comprise the humidifier outlet 5004. The water feed inlet 5206 is shown located in the inlet portion 5202a, but in other forms may be located in any one of the portions 5202a, 5202b, 5202c.

The central portion 5202b may be configured to locate and retain the heating element 5220, isolating the heating element 5220 from exposure to moisture, yet allow heat transfer to occur from the heating element 5220 to the humidifier wick 5230.

According to another aspect, the humidification chamber 5200 may further comprise an air flow baffle 5208 (as shown in FIG. 7 and FIG. 9) configured to promote turbulence in the flow and/or increase the evaporative surface area, such as by extending a length and/or a residence time during which the flow of air is in the humidification chamber 5200, for example to improve humidification performance.

In one form the air flow baffle 5208 may be as described in any one of the following patents or patent applications, the contents of which are incorporated herein by reference in their entirety: International Patent Application Publication No. WO 2015/135040 and International Patent Application Publication No. WO 2016/139645.

5.5.2.3.1 Heating Element

The amount of moisture, or absolute humidity, that a flow of air is able to retain in vapour form varies according to a temperature of the flow of air.

In some cases, the flow of air received by the humidifier 5000 may be too cold to retain adequate absolute humidity for delivery to the entrance to the airways of the patient 1000. Furthermore, delivery of cold air may cause discomfort to the patient 1000 as described above. Thus, a humidifier 5000 may comprise a heating element 5220 configured to output heat, for example to heat the flow of air. In one form, the heating element 5220 may be provided at the humidification chamber 5200, such as on the chamber housing 5202 as shown in FIG. 7 and FIG. 9. Alternatively, or additionally, the reservoir 5110 may comprise a reservoir heating element 5221 to heat water prior to it entering the humidification chamber 5200 as shown in FIG. 7.

The heating element 5220 may heat the flow of air as it passes through the humidifier 5000, as well as to assist humidification in the humidification chamber 5200 such as by heating the humidifier wick 5230. Accordingly, the heating element 5220 may be configured so that it provides sufficient thermal energy for heating and vaporisation at the highest requirements respectively, that is, where the ambient air is cold and dry.

The heating element 5220 may be configured in one of a number of ways whilst meeting the above requirements, as may be as described in any one of the following patents or patent applications, the contents of which are incorporated herein by reference in their entirety: International Patent Application Publication No. WO 2015/135040 and International Patent Application Publication No. WO 2016/139645.

5.5.2.3.2 Humidifier Wick

In one aspect of the present technology, the humidifier 5000 may comprise a water retention feature such as a humidifier wick 5230. The water retention feature (e.g. humidifier wick 5230) may be configured to retain a volume of water, which may be received from the reservoir 5110 for evaporation to humidify the flow of air before it is delivered to the patient 1000.

A humidifier wick 5230 according to the present technology may comprise a single continuous component, multiple components working as an assembly, or a discontinuous, discrete collection of wicking materials and/or elements.

A performance of the humidifier wick 5230 may degrade over time and/or usage, and in some cases the humidifier wick 5230 may no longer be suitable for use. For instance, foreign matter, such as particulates from the water, may collect or build up on the humidifier wick 5230 as it is evaporated. In some cases, collection of foreign matter may reduce water capacity and/or heat conductivity of the humidifier wick 5230. In some cases, the humidifier wick 5230 may deteriorate over time, possibly even without any use of the humidifier 5000. Still further, the foreign matter collected on the humidifier wick 5230 may be removed from the humidifier wick 5230 and be entrained onto the flow of air, which may be undesirable.

In one form, the wick 5230 may be configured to allow washing, e.g. in a dishwasher, disinfection using another agent, and/or using a microwave. Additionally, or alternatively, the humidifier wick 5230 may comprise an antimicrobial or antibacterial agent such as silver. Yet further, the humidifier 5000 may comprise self-cleaning algorithms (such as a bio-burden reduction algorithm) as will be described further below.

The wick may be shaped so that it may substantially define a part of an air path from the RPT device 4000 to the patient interface 3000. The water retention feature may wholly define a part of the air path by forming a substantially enclosed path, such as a cylindrically shaped path. In order to achieve a target level of humidification output whilst maintaining a small size for the humidifier 5000, it may be beneficial for the water retention feature to wholly define a part of the air path to maximise a contact area with the air flow. Such an arrangement may allow the water retention feature to be disposed entirely around a periphery of the air path, such that for a given length of the water retention feature the area of contact between the air path and the water retention feature is maximised. For example, the humidifier wick 5230 shown in FIG. 10 is shaped as a hollow cylinder to fit within a cylindrically shaped humidification chamber 5200, and define a cylindrically shaped, enclosed air path therethrough. It will be understood that of course, other shapes may also be suitable, for example a frustro-conical shape complementarily to a similarly shaped humidification chamber 5200, so that it would self-locate during insertion into its operating position.

In one form of the present technology the humidifier wick 5230 may be as described in any one of the following patents or patent applications, the contents of which are incorporated herein by reference in their entirety: International Patent Application Publication No. WO 2015/135040 and International Patent Application Publication No. WO 2016/139645.

Suitable materials for the humidifier wick 5230 may include (but not limited to): paper, bicomponent materials comprising hydrophilic fibres, and cellulose fibres. A humidifier wick 5230 may comprise one or more of the above listed materials in one or more arrangements (e.g. flat, corrugated, isotropic, anisotropic, layered etc.) to achieve properties of the humidifier wick 5230 described within the present document.

In one form of the present technology the humidifier wick 5230 may be made of a fibrous sheet material. In one form the fibrous sheet material may comprise a fabric woven of fibres. Such a fibrous sheet material may be configured to provide a capillary action to distribute water through the wick 5230 and retain it therein.

In one form of the present technology the fibrous sheet material may comprise different types of fibre.

In one form of the present technology the fibrous sheet material may comprise a first plurality of fibres and a second plurality of fibres, wherein the first plurality of fibres are each greater in thickness than each of the second plurality of fibres. The relatively thicker fibres may provide structural integrity to the wick as well as greater heat transference than the thinner fibres. The relatively thinner fibres may encourage waster absorption and retention due to the capillary action produced between those fibres.

In one form of the present technology the fibrous sheet material may be configured such that the relatively thicker fibres are provided closer to the heating element 5220, and the thinner fibres provided closer to the flow of air. This arrangement may encourage evaporation to occur away from the heating element 5220, thereby reducing the potential for bonding to occur between the wick 5230 and structure of the humidification chamber 5200 due to particulate build-up.

In one form of the present technology the humidifier wick 5230 may comprise one or more layers, such as a first layer and a second layer. The one or more layers may vary in form and/or functions. In one instance, the first layer may comprise the relatively thicker fibres, and the second layer may comprise the thinner fibres.

In one form of the present technology the fibrous sheet material may comprise a mono-multi woven fabric. A mono-multi woven fabric is one in which a single fibre is woven with a bundle of multiple fibres which are individually smaller in gauge than the single fibre. As an example, a suitable mono-multi woven fabric may include the TETEK™ MONO 05-1001-SK 005 produced by SEFAR.

In one form of the present technology the fibrous sheet material may comprise a mono-mono woven fabric. A mono-mono woven fabric is one in which a first single fibre is woven with a second single fibre. As an example, a suitable mono-mono woven fabric may include the TETEK™ MONO 05-1001-SK 020 produced by SEFAR. It is envisaged that the mono-mono woven fabric may be less susceptible to the build-up of water scale (residual matter following evaporation) than the mono-multi fabric, in which the bundle of multiple fibres have a greater tendency to retain particles which come in contact and are more difficult to clean as a result. The greater ease of cleaning is envisaged as having the effect of maintaining performance of the wick for a greater length of time.

The fibres may be required to withstand temperatures of substantially 80° C. without degradation, be non-reactive to common cleaning agents, and have good heat transfer properties for power efficiency purposes. Suitable materials for the fibres may include a polymer, for example polyethylene terephthalate or polypropylene.

In one form of the present technology the humidifier wick 5230 may be produced by forming the sheet material into a tubular shape, such as to conform to a shape to the humidifier chamber. In order to maintain the shape the sheet may be, for example: bonded by adhesives, or welded along a join.

5.5.2.3.3 Wick Frame

In some forms of the present technology, the humidifier 5000 may comprise a wick frame 5232, for example as shown in FIG. 10. The wick frame 5232 may be coupled to the wick 5230 (e.g. chemically bonded and/or mechanically coupled), for instance to locate and/or shape the wick 5230 (e.g. in a predetermined location and/or shape), maintain the wick 5230 in close proximity to the heating element 5220, and/or to prevent an increase in flow impedance which may occur due to a deformation of the wick 5230. The wick frame 5232 may promote, or maintain, thermal contact between the wick 5230 and the heating element 5220 by assisting in locating and/or shaping the wick 5230 as designed (e.g. by maintaining the wick 5230 in a cylindrical shape as shown in FIG. 10). In a form shown in FIG. 10, the wick frame 5232 may comprise a wick locator 5233 such as a shoulder as shown, to assist in location of the wick 5230 in relation to the wick frame 5232 in assembly.

In one form of the present technology the wick frame 5232 may be as described in any one of the following patents or patent applications, the contents of which are incorporated herein by reference in their entirety: International Patent Application Publication No. WO 2015/135040 and International Patent Application Publication No. WO 2016/139645.

5.5.2.3.4 Wick Orientation

In one form of the present technology, the humidifier 5000, or at least the humidification chamber 5200 and wick 5230 may be vertically oriented in use—i.e. a first end of the wick 5230 is above the second end of the wick.

In one form of the present technology, the humidifier 5000 may be configured such that the water feed inlet 5206 is provided at the upper end of the wick 5230, for example as illustrated in FIG. 11A. It is envisaged that this arrangement may result in gravity assisted distribution of water along the length of the wick 5230. Further, as the effect of gravity on radial distribution is removed (in comparison with horizontal orientations in which gravity draws the water towards the downwards side of the wick 5230), the radial distribution is more predictable and the build-up of residual matter is envisaged as being more even throughout the wick 5230.

In one form of the present technology, the humidifier 5000 may be configured such that the water feed inlet 5206 is provided at the lower end of the wick 5230. Such an arrangement may also assist with avoiding localised build-up of residual matter with regard to radial distribution.

5.5.2.3.5 Pre-Delivery Chamber

In one form of the present technology, the humidifier 5000 of FIG. 11A may comprise a pre-delivery chamber 5115, an example of which is shown in FIG. 11B. The pre-delivery chamber 5115 may receive and retain a volume of water from the reservoir 5110 prior to beginning delivery of water from the pre-delivery chamber 5115 to the water retention mechanism (e.g. humidifier wick 5230), in order to deliver water to the humidifier wick 5230. The pre-delivery chamber 5115 may be fluidly connected to the humidifier wick 5230 at a plurality of locations in order to evenly deliver water to the humidifier wick 5230.

In the example shown in FIG. 11B, the pre-delivery chamber 5115 is formed by capping the chamber housing 5202 with a moulded cap 5518, and welding the cap 5518 in place at weld joint 5520. In FIG. 11B, the air flow baffle 5208 bears against the cap 5518, and comprises a lateral flange 5522 extending radially to the wick 5230.

The surface of the flange 5522 facing the interior of the pre-delivery chamber 5115 pitches up between an inner position 5524 and an outer position 5526 next to the wick 5230. This produces a depression in which a predetermined amount of water pools before communication of water can occur from the pre-delivery chamber 5115 to the humidifier wick 5230 via a lateral opening 5528.

In one form of the present technology the pre-delivery chamber 5115 may be as described in any one of the following patents or patent applications, the contents of which are incorporated herein by reference in their entirety: International Patent Application Publication No. WO 2015/135040 and International Patent Application Publication No. WO 2016/139645.

5.5.2.4 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 12. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.5.2.4.1 Pressure Transducer

One or more pressure transducers 5212 may be provided to the humidifier 5000 in addition to, or instead of, a pressure sensor 4272 provided in the RPT device 4000.

5.5.2.4.2 Flow Rate Transducer

One or more flow rate transducers 5214 may be provided to the humidifier 5000 in addition to, or instead of, a flow rate sensor 4274 provided in the RPT device 4000.

5.5.2.4.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.5.2.4.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.5.2.5 Humidifier Controller

According to one arrangement of the present technology, a humidifier 5000 may comprise a humidifier controller 5250 as shown in FIG. 12. In one form, the humidifier controller 5250 may be a part of the central controller 4230.

In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 12, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

Various humidifier algorithms may be implemented by the humidifier controller 5250 as described in any one of the following patents or patent applications, the contents of which are incorporated herein by reference in their entirety: International Patent Application Publication No. WO 2015/135040 and International Patent Application Publication No. WO 2016/139645.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Patient: A person, whether or not they are suffering from a respiratory disease.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.6.1.1 Holes

A surface may have a one-dimensional hole, e.g. a hole bounded by a plane curve or by a space curve. Thin structures (e.g. a membrane) with a hole, may be described as having a one-dimensional hole.

A structure may have a two-dimensional hole, e.g. a hole bounded by a surface. For example, an inflatable tyre has a two dimensional hole bounded by the inside surface of the tyre. In another example, a bladder with a cavity for air or gel could have a two-dimensional hole. In a yet another example, a conduit may comprise a one-dimension hole (e.g. at its entrance or at its exit), and a two-dimension hole bounded by the inside surface of the conduit.

5.7 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.8 Reference Signs List

| | |
|---|---|
| patient | 1000 |
| bed partner | 1100 |
| patient interface | 3000 |
| seal-forming structure | 3100 |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| pneumatic components | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| heated air circuit | 4171 |
| supplemental oxygen | 4180 |
| electrical components | 4200 |
| Printed Circuit Board Assembly | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| therapy control module | 4330 |
| humidifier | 5000 |
| humidifier inlet | 5002 |
| humidifier outlet | 5004 |
| reservoir | 5110 |
| water volume detector | 5112 |
| pre-delivery chamber | 5115 |
| water delivery mechanism | 5150 |
| water pump | 5152 |
| water delivery conduit | 5154 |
| mechanism | 5156 |
| water check valve | 5158 |
| deioniser cartridge | 5160 |
| base portion | 5164 |
| cartridge outlet | 5166 |
| first end wall | 5168-1 |
| second end wall | 5168-2 |
| first side wall | 5170-1 |
| second side wall | 5170-2 |
| lid | 5172 |
| cartridge inlet | 5174 |
| handle | 5176 |
| filter frame | 5178 |
| frame legs | 5180 |
| upper frame member | 5182 |
| mesh | 5184 |
| first baffle | 5186-1 |
| second baffle | 5186-2 |
| third baffle | 5186-3 |
| arrow | 5188 |
| seal recess | 5190 |
| seal | 5192 |

| -continued | |
|---|---|
| humidification chamber | 5200 |
| chamber housing | 5202 |
| inlet portion | 5202a |
| central portion | 5202b |
| outlet portion | 5202c |
| water filter | 5204 |
| water feed inlet | 5206 |
| air flow baffle | 5208 |
| humidifier transducer | 5210 |
| air pressure sensor | 5212 |
| flow rate transducers | 5214 |
| temperature sensor | 5216 |
| temperature transducers | 5216 |
| humidity sensors | 5218 |
| humidity sensor | 5218 |
| heating element | 5220 |
| reservoir heating element | 5221 |
| humidifier wick | 5230 |
| wick frame | 5232 |
| wick locator | 5233 |
| heating element | 5240 |
| humidifier controller | 5250 |
| central humidifier controller | 5251 |
| heating element controller | 5252 |
| air circuit controller | 5254 |
| cap | 5518 |
| joint | 5520 |
| flange | 5522 |
| lateral flange | 5522 |
| inner position | 5524 |
| outer position | 5526 |
| lateral opening | 5528 |
| humidifier controller | 5550 |

The invention claimed is:

1. A humidifier for use with a respiratory pressure therapy (RPT) device that is configured to pressurize and direct a flow of air to an entrance to the airways of a patient for treatment of a respiratory disorder, the humidifier being configured to increase the absolute humidity of the pressurized flow of air, the increase being compared to the absolute humidity of ambient air, the humidifier comprising:
a reservoir configured to hold a first volume of liquid; and
a humidifier chamber comprising:
a humidifier inlet configured to receive the pressurized flow of air;
a humidifier outlet configured to direct the pressurized flow of air out of the humidifier chamber;
a humidifier wick configured to retain a second volume of liquid and at least partly form a flow path for the pressurized flow of air that flows from the humidifier inlet to the humidifier outlet during use; and
a heating element configured to heat the humidifier wick to vapourise the second volume of liquid to add absolute humidity to the pressurized flow of air that flows along the flow path during use; and
wherein the humidifier wick comprises a fibrous sheet material, the fibrous sheet material comprising a fabric woven of fibres,
wherein the fabric woven of fibres comprises a first plurality of fibres and a second plurality of fibres, the first plurality of fibres being different from the second plurality of fibres in at least one aspect,
wherein the first plurality of fibres are each greater in thickness than each of the second plurality of fibres, and
wherein the first plurality of fibres are positioned closer to the heating element than the second plurality of fibres, and the second plurality of fibres are positioned closer to the pressurized flow of air than the first plurality of fibres.

2. The humidifier of claim 1, wherein the fibrous sheet material is configured to distribute water through the humidifier wick via capillary action and retain it therein.

3. The humidifier of claim 1, wherein the fibrous sheet material comprises a first layer comprising the first plurality of fibres, and a second layer comprising the second plurality of fibres.

4. The humidifier of claim 1, wherein the fabric woven of fibres is a mono-multi woven fabric.

5. The humidifier of claim 1, wherein the fabric woven of fibres is a mono-mono woven fabric.

6. The humidifier of claim 1, wherein the humidifier wick is tubular in shape.

7. An RPT system for treating a respiratory disorder comprising:
an RPT device configured to pressurize and direct a flow of air to an entrance to the airways of a patient for treatment of the respiratory disorder, the RPT device comprising a Positive Airway Pressure generator configured to pressurize the flow of air; and
the humidifier of claim 1 in fluid communication with the RPT device via the humidifier inlet.

8. The humidifier of claim 1, further comprising:
a water feed inlet configured to direct the first volume of liquid to the humidifier wick; and
a deioniser positioned upstream of the water feed inlet and configured to deionise the first volume of liquid prior to vapourisation in the humidifier wick.

9. The humidifier of claim 8, wherein the deioniser is provided within the reservoir.

10. The humidifier of claim 8, wherein the deioniser comprises at least one ion exchange resin.

11. The humidifier of claim 10, wherein the deioniser comprises a first type of resin configured to remove positively charged ions from the first volume of liquid and a second type of resin configured to remove negatively charged ions from the first volume of liquid.

12. The humidifier of claim 10, wherein the deioniser comprises a removable deioniser cartridge configured to hold at least one ion exchange resin.

13. A wick for positioning within a humidifier chamber of an apparatus to increase the absolute humidity of a pressurized flow of air for delivery to an entrance to the airways of a patient for treatment of a respiratory disorder, the increase being compared to the absolute humidity of ambient air,
wherein the wick is configured to retain a volume of water,
wherein the wick comprises a fibrous sheet material, wherein the fibrous sheet material further comprises a fabric woven of fibres,
wherein the fibrous sheet material comprises a first plurality of fibres and a second plurality of fibres,
wherein the first plurality of fibres are each greater in thickness than each of the second plurality of fibres, and
wherein, in use, the fibrous sheet material is configured such that the first plurality of fibres are positioned closer to a heating element of the apparatus than the second plurality of fibres, and the second plurality of fibres are positioned closer to the pressurized flow of air than the first plurality of fibres.

14. The wick of claim 13, wherein the fibrous sheet material is configured to distribute water through the wick via capillary action and retain it therein.

15. The wick of claim 13, comprising a first layer comprising the first plurality of fibres, and a second layer comprising the second plurality of fibres.

16. The wick of claim 13, wherein the fabric woven of fibres is a mono-multi woven fabric.

17. The wick of claim 13, wherein the fabric woven of fibres is a mono-mono woven fabric.

18. The wick of claim 13, wherein the wick is tubular in shape.

* * * * *